United States Patent
Acemoglu et al.

(10) Patent No.: US 7,371,865 B2
(45) Date of Patent: May 13, 2008

(54) PROCESS FOR THE MANUFACTURE OF HMG-COA REDUCTASE INHIBITORS

(75) Inventors: Murat Acemoglu, Basel (CH); Bernhard Riss, Huningue (FR)

(73) Assignee: Novartis Pharmaceuticals Corporation, East Hanover, NJ (US)

( * ) Notice: Subject to any disclaimer, the term of this patent is extended or adjusted under 35 U.S.C. 154(b) by 315 days.

(21) Appl. No.: 10/502,177

(22) PCT Filed: Jan. 30, 2003

(86) PCT No.: PCT/EP03/00954

§ 371 (c)(1), (2), (4) Date: Jul. 21, 2004

(87) PCT Pub. No.: WO03/064392

PCT Pub. Date: Aug. 7, 2003

(65) Prior Publication Data

US 2005/0070605 A1    Mar. 31, 2005

Related U.S. Application Data

(60) Provisional application No. 60/353,787, filed on Jan. 31, 2002.

(51) Int. Cl.
C07D 215/04 (2006.01)
C07D 209/04 (2006.01)
(52) U.S. Cl. ..................... 546/173; 548/490
(58) Field of Classification Search ........... 546/173; 548/490
See application file for complete search history.

(56) References Cited

U.S. PATENT DOCUMENTS

| 4,650,890 | A | * | 3/1987 | Jewell et al. | 556/446 |
|---|---|---|---|---|---|
| 5,034,399 | A | | 7/1991 | Hübsch et al. | 514/300 |
| 5,049,577 | A | | 9/1991 | Varma et al. | 514/414 |
| 5,354,772 | A | | 10/1994 | Kathawala | 514/311 |
| 5,856,336 | A | | 1/1999 | Fujikawa et al. | 514/409 |
| 6,528,661 | B2 | * | 3/2003 | Niddam et al. | 548/537 |
| 6,835,838 | B2 | * | 12/2004 | Chen et al. | 546/173 |
| 6,909,003 | B2 | * | 6/2005 | Storz | 546/152 |
| 6,965,031 | B2 | * | 11/2005 | Hara | 546/136 |
| 7,064,209 | B2 | * | 6/2006 | Horiuchi et al. | 546/173 |

FOREIGN PATENT DOCUMENTS

| EP | 0 304 063 B1 | 2/1989 |
|---|---|---|
| EP | 0 340 007 | 11/1989 |
| EP | 0 520 406 B1 | 12/1992 |

OTHER PUBLICATIONS

Cohen and Khedouri, vol. 83, pp. 4228-4233.
Heathcock et al., "Total Synthesis and Biological Evaluation of Structural Analogues of Compactin and dihydromevinolin", *J Med Chem*, vol. 30, No. 10, pp. 1858-1873 (1980).
Karanewsky, Malley and Gougoutas, "Practical Synthesis of an Enantiomerically Pure Synthon for the Preparation of Mevinic Acid Analogues", *J Org Chem*, vol. 56, No. 11, pp. 3744-3747 (1991).
Matsumura, Hashiguchi, Ikariya and Noyori, "Asymmetric Transfer Hydrogenation of α,β-Acetylenic Ketones", *J Am Chem Soc*, vol. 119, No. 37, pp. 8738-8739 (1997).
Ozegowski, Kunath and Schick, "Lipase-Catalyzed Asymmetric Alcoholysis of 3-Substituted Pentanedioic Anhydrides", *Liebigs Ann Chem*, pp. 805-808 (1993).
Rosen, Wantanabe and Heathcock, "A Convenient Assay for the Optical Purity of Monmethyl 3-Hydroxypentanedioate", *J Org Chem*, vol. 49, No. 19, pp. 3657-3659 (1984).
Suzuki et al., "First Systematic Chiral Syntheses of Two Pairs of Enantiomers with 3,5-Dihydroxyheptenoic Acid Chain, Associated with a Potent Synthetic Statin NK-104", *Bioorg Med Chem Lett*, vol. 9, No. 20, pp. 2977-2982 (1999).
Theisen and Heathcock, "Improved Procedure for Preparation of Optically Active 3-Hydroxyglutarate Monoesters and 3-Hydroxy-5-oxoalkanoic Acids", *J Org Chem*, vol. 53, No. 10, pp. 2374-2378 (1988).
Vries et al., "The Family Approach to the Resolution of Racemates", *Angew Chem Int Ed*, vol. 37, No. 17, pp. 2349-2354 (1998).

* cited by examiner

*Primary Examiner*—D. Margaret Seaman
(74) *Attorney, Agent, or Firm*—Patrick H. Higgins; Eckert Seamans Cherin & Mellott, LLC

(57) ABSTRACT

The invention relates to a process for the manufacture of a compound of formula

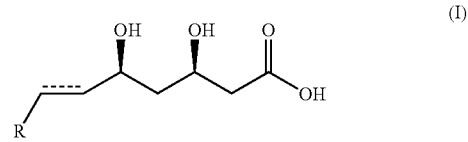

(I)

or a salt, especially a pharmaceutically acceptable salt with a base, thereof or a lactone thereof wherein the element ⁝⁝⁝⁝ represents —$CH_2$—$CH_2$— or —CH=CH— and R represents a cyclic residue.

12 Claims, No Drawings

PROCESS FOR THE MANUFACTURE OF HMG-COA REDUCTASE INHIBITORS

The invention relates to a process for the manufacture of enantiomerically pure HMG-CoA reductase inhibitors, to process steps and to novel intermediates.

HMG-CoA reductase inhibitors (also called β-hydroxy-β-methylglutaryl-co-enzyme-A reductase inhibitors and also called statins) are understood to be those active agents which may be preferably used to lower the lipid levels including cholesterol in blood and can be used e.g. for the prevention or treatment of hyperlipidemia and artheriosclerosis.

The class of HMG-Co-A reductase inhibitors comprises compounds having differing structural features. For example, mention may be made of the compounds which are selected from the group consisting of atorvastatin, cerivastatin, fluvastatin, lovastatin, pitavastatin (formerly itavastatin), pravastatin, rosuvastatin, and simvastatin, or, in each case, a pharmaceutically acceptable salt thereof.

Preferred HMG-Co-A reductase inhibitors are those agents which have been marketed, most preferred is fluvastatin, atorvastatin, pitavastatin, especially the Calcium salt thereof, or simvastatin or a pharmaceutically acceptable salt thereof.

Atorvastatin of formula

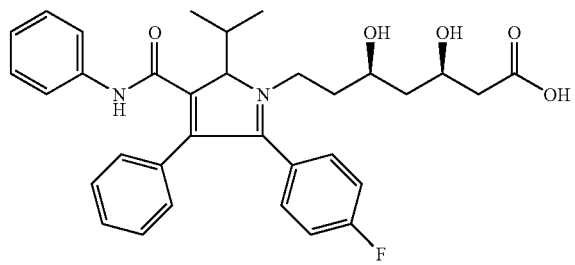

is disclosed and claimed in U.S. Pat. No. 5,273,995.

Cerivastatin of formula

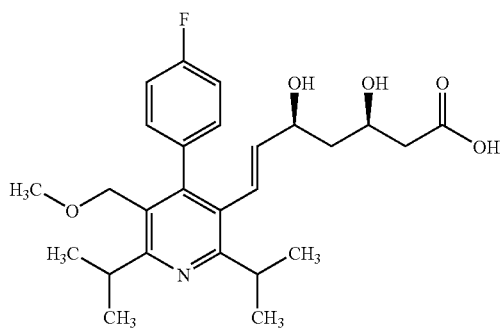

is disclosed and claimed in U.S. Pat. No. 5,177,080.

Racemic fluvastatin with syn-configuration of the hydroxy groups in formula

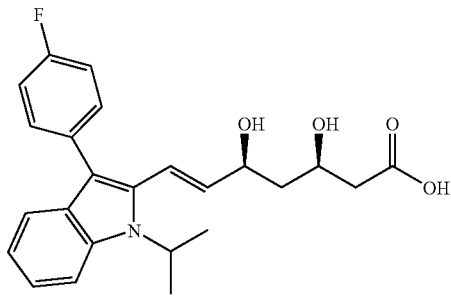

is disclosed and claimed in U.S. Pat. No. 5,345,772.

Lovastatin of formula

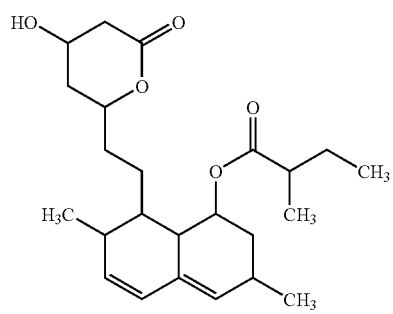

is disclosed and claimed in U.S. Pat. No. 4,231,938.

Pitavastatin of formula

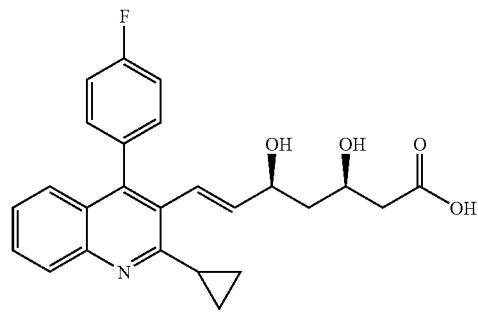

is disclosed and claimed in U.S. Pat. No. 5,856,336.

Pravastatin of formula

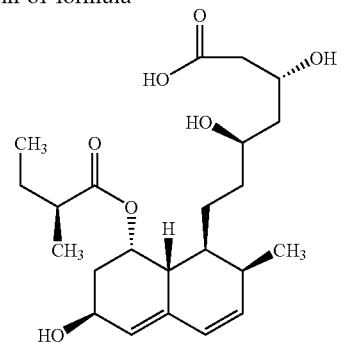

is disclosed and claimed in U.S. Pat. No. 4,410,629.

Rosuvastatin of formula

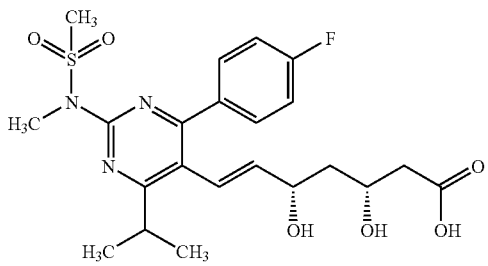

is disclosed and claimed in U.S. Pat. No. 5,260,440.

Simvastatin of formula

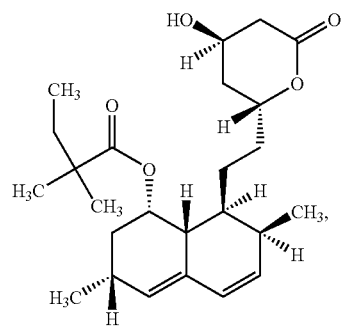

is disclosed and claimed in U.S. Pat. No. 4,444,784.

The structure of the active agents identified hereinbefore or hereinafter by generic or tradenames may be taken from the actual edition of the standard compendium "The Merck Indee" or from databases, e.g. Patents International or Life-Cycle Patents International, respectively, (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

Acidic representatives of HMG-Co-A reductase inhibitors have been launched are being developed as salts, for example, fluvastatin as sodium salt and pitavastatin as calcium salt.

The corresponding active ingredients or a pharmaceutically acceptable salts thereof may also be used in form of a solvate, such as a hydrate or including other solvents, used for crystallization.

Essentially, statins comprise a cyclic core element and a side chain element of formula

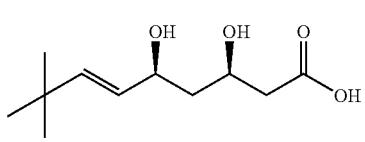

(a 3,5-dihydroxy-hept-6-enoic acid moiety) that might form a corresponding lactone partial structure of formula

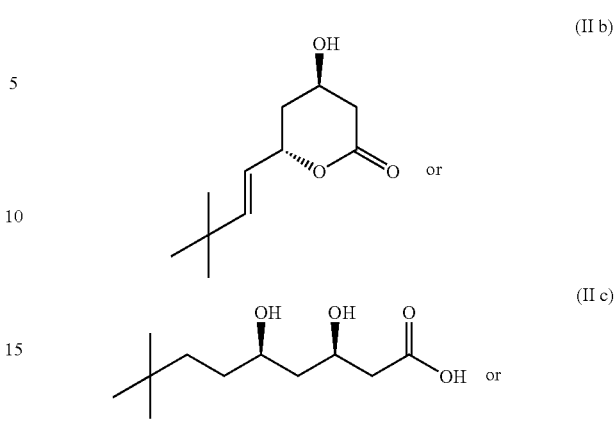

(a 3,5-dihydroxy-heptanoic acid derivative) that might form a corresponding lactone partial structure of formula

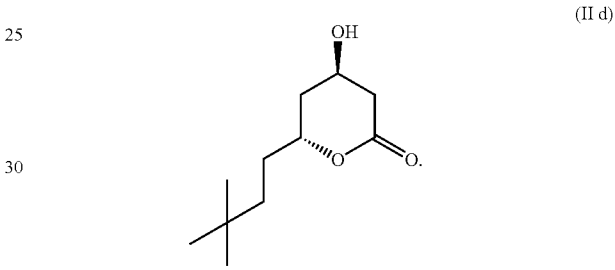

In said side chain elements (II a) or (II c), respectively, the 3,5-syn diol structure and the R-configuration at C-3 are essential features, as corresponding statins with this specific element exhibit the highest biological activity.

The objective of the present invention is to provide an enantioselective synthesis of compounds of formula (I) resulting in high yields and moreover guaranteeing a minimization of the ecological pollution of the environment, being economically attractive, e.g. by using less reaction steps in the reaction sequence for the manufacture of compounds of formula I, and leading to largely enantiomerically pure target products and to products of high crystallisability. Furthermore, another objective of the present invention is to provide a process that can be carried out in a larger scale and can thus be used for a corresponding production process. Furthermore, there is a need to avoid any separation and disposal of any stereoisomers.

Surprisingly, the process of the present invention clearly meets the above objectives. The process relates to an enantioselective synthesis by using essentially the so-called Wittig-Wadsworth-Emmons (Wittig-Homer) or Wittig condensation via chemical desymmetrisation. For example, an enantiomeric excess (ee) of a compound of formula (I) or a salt thereof of ≧95%, preferably ≧98% and most preferably ≧99% can be achieved. Moreover an ee of ≧99.5% can easily be obtained. Furthermore, according to the present invention, a diasteromeric excess (de) of ≧95%, preferably ≧98% and most preferably ≧99% can easily be achieved for a compound of formula (I) or a salt thereof obtained according to the present invention.

The invention relates to a process for the manufacture of an enantiomerically pure form of a HMG-CoA reductase inhibitory mevalonic acid derivative of formula (I)

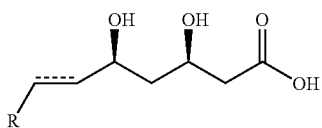

or a salt, especially a pharmaceutically acceptable salt with a base, thereof or a lactone thereof, wherein the element ······ represents —$CH_2$—$CH_2$— or —CH=CH— and R represents a cyclic residue.

A salt of a compound of formula (I) is, for example, a salt with a base, preferably a corresponding pharmaceutically acceptable salt thereof.

A lactone of a compound of formula (I) is represented by formula (I a)

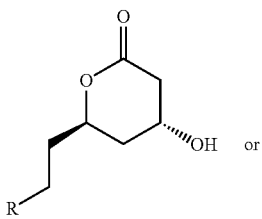

or

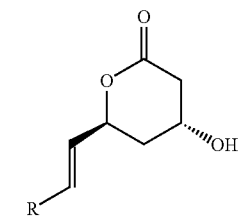

Corresponding cyclic residue R comprises a cyclic residue selected from the group consisting of

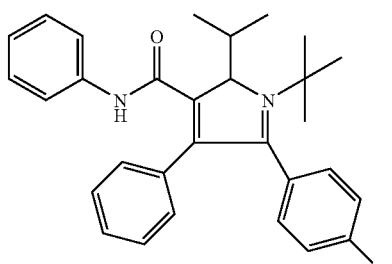

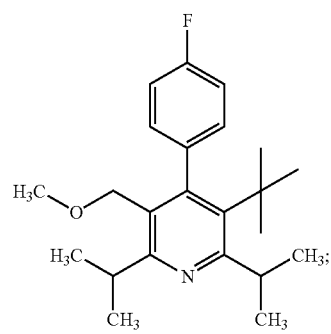

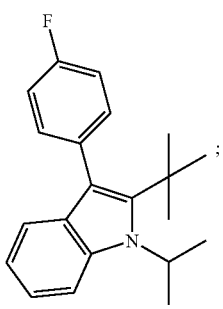

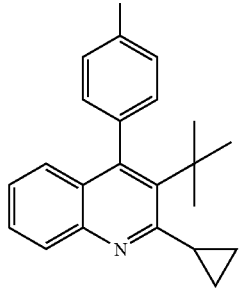

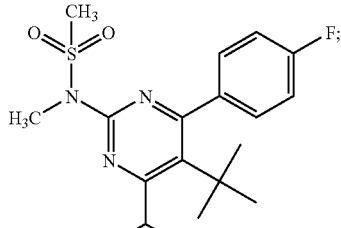

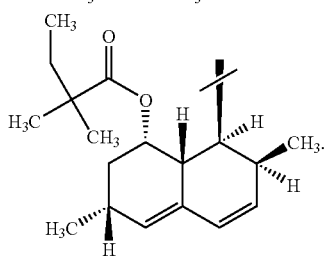

Extensive experimental evaluations surprisingly resulted in a process sequence for the manufacture that meets the above criteria showing the indicated advantages.

Compared to the process as disclosed in J.Org.Chem. 1991, 56,3744-3747, it has been surprisingly found that the process according to the present invention can be simplified by omitting (i) the oxidation step with $N_2O_4$ forming the corresponding N-nitrosamine and (ii) the hydrolysis to form of the free acid and (iii) the methylation to form the methylester.

It has been proven, that the reaction sequence according to the present invention, especially when using corresponding starting material and Intermediates exhibiting the amide function wherein the amide element is repesented by formula

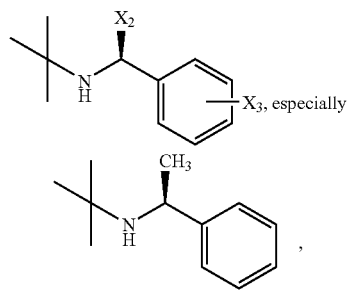

for example, instead of using a corresponding ester exhibiting the alkoholic element of formula

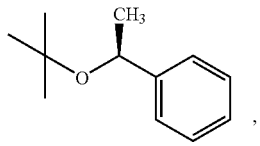

leads to the above-mentioned advantages.

Furthermore, in a recent publication [Bioorg. Med. Chem. Lett. 9 (1999) 2977-2982)] an improved process for the manufacture of pitavastatin has been disclosed describing the step-by-step formation of the side chain of formula (II a) resulting in a mixture of diastereomers that need to be separated. Consequently, one half of the diastereomer cannot be used. In opposite to said procedure, the process of the present invention is clearly more economic.

The process for the manufacture of an enantiomerically pure form of a compound of formula

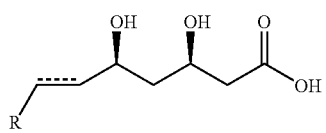

or a salt thereof according to the present inventions is characterized by (a) reacting compounds (IIIa) or (IIIb)

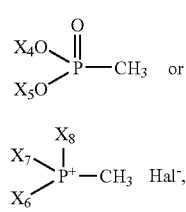

wherein $X_4$ and $X_5$, independently of one another, represents $C_1$-$C_7$-alkyl or phenyl-$C_1$-$C_7$-alkyl;

$X_6$, $X_7$ and $X_8$, Independently of one another, represent phenyl that is unsubstituted or substituted by one or more substituents selected from the group consisting of $C_1$-$C_7$alkyl, hydroxy, $C_1$-$C_7$alkoxy, $C_2$-$C_8$alkanoyl-oxy, halogen, nitro, cyano, and $CF_3$; and Hal⁻ represents a halide anion;

with a metallated alkane to form the corresponding ylide and then reacting the resulting ylide intermediate with a compound of formula

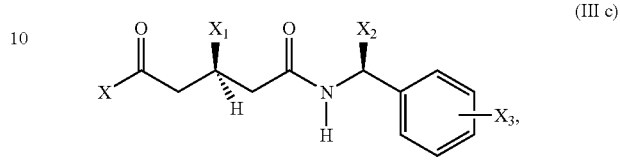

wherein
X represents etherified hydroxy, esterified hydroxy, or unsubstituted or mono- or di-substituted amino;
$X_1$ is protected hydroxy;
$X_2$ represents $C_1$-$C_7$alkyl; and
$X_3$ represents hydrogen or one or more substituents, e.g. selected from the group consisting of $C_1$-$C_7$alkyl, hydroxy, $C_1$-$C_7$alkoxy, $C_2$-$C_8$alkanoyl-oxy, halogen, nitro, cyano, and $CF_3$;

(b) optionally, if desired, converting a resulting compound of formula (III d)

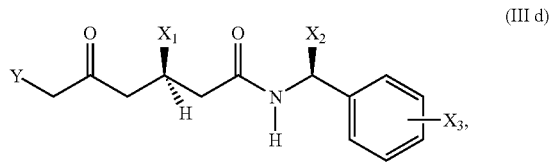

wherein $X_1$, $X_2$ and $X_3$ have the meanings as defined above and Y represents a group of formula $(X_4O)(X_5O)P(=O)$— or $(X_6)(X_7)(X_8)P^+$ Hal⁻ and $X_4$, $X_5$, $X_6$, $X_7$, $X_8$ and Hal⁻ have the meanings as defined above;
into a compound of formula (III e)

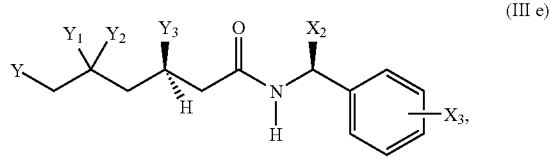

wherein $X_2$, $X_3$ and Y, have the meaning as defined above and wherein
$Y_1$ represents hydroxy or protected hydroxy and $Y_2$ is hydrogen and $Y_3$ is hydroxy or protected hydroxy, and $Y_1$ and $Y_3$ forming a syn-diol configuration; or wherein
$Y_1$ and $Y_3$ together represent —O-Alk-O— and Alk being $C_1$-$C_7$alkylidene; and $Y_2$ is hydrogen, and $Y_1$ and $Y_3$ forming a syn-diol configuration;.

(c) reacting a compound of formula (III e)
wherein $X_2$, $X_3$ and Y, have the meaning as defined above and wherein
$Y_1$ represents hydroxy or protected hydroxy and $Y_2$ is hydrogen and $Y_3$ is hydroxy or protected hydroxy, and $Y_1$ and $Y_3$ forming a syn-diol configuration; or wherein $Y_1$ and $Y_3$ together represent —O-Alk-O— and Alk being $C_1$-$C_7$alkylidene; and $Y_2$ is hydrogen, and $Y_1$ and $Y_3$ forming a syn-diol configuration; or wherein $Y_1$ and $Y_2$ together represent the oxo group and $Y_3$ represents protected hydroxyl (corresponding to compounds of formula (II d);

with an aldehyde of formula (III f) R—CH(=O) resulting in a compound of formula (III g)

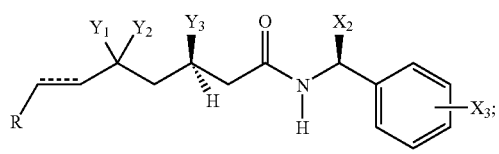

(III g)

wherein R, $X_2$, $X_3$, $Y_1$, $Y_2$ and $Y_3$ and the element ----- have the meanings as definied above;

if desired, reducing corresponding compounds of formula (III g), wherein the element ----- is —CH=CH— to result in a compound wherein said element is —CH$_2$—CH$_2$—; and (d) if a compound of formula (III g) is obtained, wherein one of $Y_1$ and $Y_3$ is protected hydroxy and the other is hydroxy or both of $Y_1$ and $Y_3$ is protected hydroxy and, in each case $Y_2$ is hydrogen; and $Y_1$ and $Y_3$ are forming the syn configuration; or $Y_1$ and $Y_3$ together represent —O-Alk-O— and Alk being $C_1$-$C_7$alkylidene and $Y_1$ and $Y_3$ are forming the syn configuration; and $Y_2$ is hydrogen; or by removing the hydroxy protection group(s) to a compound of formula

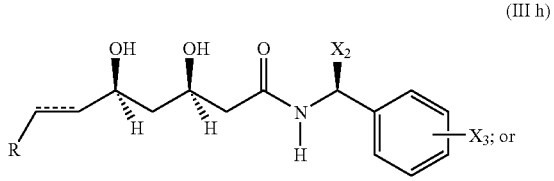

(III h)

if desired, reducing corresponding compounds of formula (III h), wherein the element ----- is —CH=CH— to result in a compound wherein said element is —CH$_2$—CH$_2$—;

(e) if a compound of formula (III g) is obtained, wherein $Y_1$ and $Y_2$ together form the oxo group =O; and $Y_3$ is protected hydroxy ($X_1$); converting said compound of formula (III g), to a compound of formula (III i)

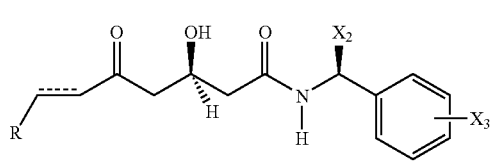

(III i)

by removing the hydroxy protection group;

wherein R, $X_2$, $X_3$ and the element ----- have the meanings as definied above; and subsequent reduction of said compound of formula (III i) to a compound of formula (III h);

(f) hydrolyzing a compound of formula (III h) to a compound of formula (I) or a salt thereof and (g) isolating a resulting compound of formula (I) or a salt thereof;

and, if desired, converting a resulting free acid of formula (I) into a salt thereof or into a lactone of formula (I a) or (I b), respectively, or converting a resulting lactone of a formula (I a) or (I b) into an acid of formula (I) or a salt thereof.

Most preferably, in compounds of formulae (III c), (III d), (III e), (III g), (III h) and (III i), in each case $X_2$ is methyl and $X_3$ is hydrogen.

According to the present process described above and hereinafter any of both enantiomers can be prepared, for example, by using either a compound of formula (III c'''') or its enantiomer for the desymmetrisation step. Furthermore, by applying the racemic mixture of a compound of formula (III c''''), racemic forms of the said HMG-CoA reductase inhibitors can be obtained.

The general terms used hereinbefore and hereinafter have the following meanings, unless defined otherwise.

Etherified hydroxy is, for example, $C_1$-$C_7$alkoxy, ar-$C_1$-$C_7$alkoxy, $C_3$-$C_8$cycloalkoxy, $C_3$-$C_8$-cycloalkyl-$C_1$-$C_7$alkoxy.

Esterified hydroxy is, for example, R—CO—O, aroyloxy, $C_2$-$C_8$-alkanoyloxy, or ar-$C_2$-$C_8$-alkanoyloxy.

In mono- or di-substituted amino the amino group is mono-substituted or, independently of one another, di-substituted by a substituent selected from the group consisting of $C_1$-$C_7$alkoxy, $C_1$-$C_7$alkyl, ar-$C_1$-$C_7$alkyl, $C_3$-$C_8$-cycloalkyl, $C_3$-$C_8$-cycloalkyl-$C_1$-$C_7$alkyl.

$C_1$-$C_7$Alkoxy is for example methoxy, ethoxy, n-propyloxy, isopropyloxy, n-butyloxy, isobutyl-oxy, sec-butyloxy, tert-butyloxy or a corresponding pentyloxy, hexyloxy, or heptyloxy residue. $C_1$-$C_4$alkoxy is preferred. Methoxy is especially preferred.

$C_1$-$C_7$Alkyl is for example methyl, ethyl, n-propyl, isopropyl, n-butyl, isobutyl, sec-butyl, tert-butyl or a corresponding pentyl, hexyl or heptyl residue. $C_1$-$C_4$alkyl, especially methyl, is preferred.

$C_3$-$C_8$cycloalkoxy and $C_3$-$C_8$cycloalkoxy in $C_3$-$C_8$cycloalkoxy-$C_1$-$C_7$alkyl is preferably $C_3$-$C_6$cycloalkoxy, for example, cyclopropoxy, cyclopentoxy or cyclohexyloxy.

$C_3$-$C_8$cycloalkyl is in particular $C_3$-$C_6$cycloalkyl, such as cyclopropyl, cyclobutyl, cyclopentyl, or cyclohexyl. Cyclopropyl is especially preferred.

$C_2$-$C_8$Alkanoyl in $C_2$-$C_8$alkanoyl-oxy is in particular acetyl, propionyl, butyryl, isobutyryl or pivaloyl. $C_2$-$C_5$Akanoyl is preferred.

Halogen is in particular halogen with an atomic number up to and including 35, i.e. fluorine, chlorine or bromine, and in a broader sense includes iodine. Fluorine or chlorine is preferred.

Phenyl-$C_1$-$C_7$alkyl is in particular phenyl-$C_1$-$C_4$alkyl, such as benzyl or 1- or 2-phenethyl.

$C_1$-$C_7$Alkylidene is in particular metyhlen, ethylidene, 1,1- or 2,2-propylidene, also 1,1- or 2,2-butylidene or 1,1-, 2,2- or 3,3-pentylidene. $C_2$-$C_5$alkylidene is preferred.

Protected hydroxy ($X_2$ and/or $X_4$) represents silyloxy, esterified or etherified hydroxy, tetrahydropyranyloxy. Silyloxy is, for example, tri-$C_1$-$C_7$alkyl-silyloxy, especially tert-butyl-dimethyl-silyloxy.

$C_1$-$C_7$Alkylene is preferably $C_1$-$C_4$alkylene, for example, methylene, 1,2-ethylene, 1,2- or 1,3-propylene and also comprises $C_2$-$C_7$alkylidene, preferably $C_2$-$C_4$alkylene, for example, 1,1-ethylene, 1,1- or 2,2-propylidene. Most preferred is 2,2-propylidene.

The aryl residue (ar) is preferably carbocyclic aryl, such as phenyl, biphenylyl or naphthtyl, or heterocyclic aryl, such as pyridyl. Corresponding are unsubstituted or substituted by one or more, e.g. two or three, residues e.g. those selected from the group consisting of $C_1$-$C_7$alkyl, hydroxy, $C_1$-$C_7$alkoxy, $C_2$-$C_8$alkanoyl-oxy, halogen, nitro, cyano, and $CF_3$.

The reactions described above and below in the variants are carried out, for example in the absence or, customarily, in the presence of a suitable solvent or diluent or a mixture thereof, the reaction, as required, being carried out with cooling, at room temperature or with warming, for example in a temperature range from about −80° C. up to the boiling point of the reaction medium, preferably from about −10° to about +200° C., and, if necessary, in a closed vessel, under pressure, in an inert gas atmosphere and/or under anhydrous conditions.

Step (a):

In reaction Step (a), the reaction of a compound of formula (III a) or (III b), respectively, with a metallated alkane is carried out in an inert solvent, such as an ether, preferably tetrahydrofuran, and at low temperatures, for example, from −78° to 0° C., preferably at −78° C. The subsequent addition of a compound of formula (III c) is effected under the same reaction conditions, preferably in the solvent tetrahydrofuran and at −78° C.

Preferred X is $C_1$-$C_7$alkoxy, especially, methoxy or ethoxy, or N—$C_1$-$C_7$alkyl-N—$C_1$-$C_7$alkoxy-amino, most preferably N-methyl-N-methoxy-amino. Corresponding N—$C_1$-$C_7$alkyl-N—$C_1$-$C_7$alkoxy-amino derivatives are novel.

Accordingly, the present invention also relates to a compound of formula (III c), wherein X represents N—$C_1$-$C_7$alkyl-N—$C_1$-$C_7$alkoxy-amino, most preferably N-methyl-N-methoxy-amino.

Metallated alkanes are, for example, alkane alkalimetalls, such as butyl lithium or hexyl lithium etc. A preferred metallated alkane is butyl lithium.

Step (b)

$X_4$ and $X_5$ are, in each case, preferably $C_1$-$C_7$alkyl, especially $C_1$-$C_4$alkyl, most preferably methyl or ethyl.

$X_6$, $X_7$ and $X_8$ are, in each case, preferably, phenyl.

Halide Hal⁻ is preferably chloride, but also bromide and iodide.

Preferred is the reaction with a compound of formula (III a).

For the manufacture of a compound of formula (III e), wherein $X_2$, $X_3$ and Y, have the meaning as defined above and wherein $Y_1$ represents hydroxy or protected hydroxy and $Y_2$ is hydrogen and $Y_3$ is hydroxy or protected hydroxy, and $Y_1$ and $Y_3$ forming a syn-diol configuration; a corresponding compound of formula (III e), wherein $Y_1$ and $Y_2$ together form the oxo group, is reduced with a suitable reduction agent.

The reduction is carried our with an appropriate reduction agent, for example, by catalytic hydrogenation in the presence of a hydrogenation catalyst, for example, a Ruthenium catalyst, such as (Ru(cod)(nu-3-(2-methylally))2, by reduction with a hydride, for example, a hydride which, if desired, may be complex, such as a hydride formed from an element of the 1st and 3rd main groups of the periodic table of the elements, for example borohydride or aluminohydride, for example lithium borohydride, lithium aluminium hydride, diisobutylaluminium hydride (an additional reduction step using alkali metal cyanoborohydride, such as sodium cyanoborohydride, may be necessary), and also diborane.

A preferred reduction agent is, for example, a hydride, for example, an alkalimetal borohydrid, especially sodium borohydride, preferably in the presence of a di-$C_1$-$C_7$alkyl-$C_1$-$C_7$alkoxy-borane, most preferably diethyl-methoxy-borane.

The reduction is carried out in an inert solvent, such as an ether, preferably tetrahydrofuran, and at low temperatures, for example, from −78° to 0° C., preferably at −78° C. To split a corresponding boronic ester the reaction mixture is then oxidized with an oxidizing agent, such as a peroxide, especially, hydrogen peroxide. The oxidation is carried out in an inert solvent, such as a nitrile, preferably acetonitrile, and in a temperature range from, for example, from 0° C., to the boiling point of the solvent, preferably in a range of 20° to 50° C.

If desired, in a resulting compound of formula (III e), wherein $Y_1$ represent hydroxy and $Y_2$ is hydrogen, the hydroxy group $Y_1$ is protected, for example, by reacting with an halide, for example an halide of formula $Y_1$-Hal and Hal being halogen, especially, chloride, bromine or iodide.

If desired, in a resulting compound of formula (III e), wherein $Y_1$ represents hydroxy and $Y_2$ is hydrogen, the protected hydroxy group $X_1$ is removed, for example, by treatment with a strong acid, such as a mineral acid, e.g. $H_3PO_4$. Especially, an etherified or esterified hydroxy group or a silyloxy group is split by treatment with an acid.

For the manufacture of a compound of formula (III e), wherein $X_2$, $X_3$ and Y, have the meaning as defined above and wherein $Y_1$ and $Y_3$ together represent —O-Alk-O— and Alk being $C_1$-$C_7$alkylidene; and $Y_2$ is hydrogen, and $Y_1$ and $Y_3$ forming a syn-diol configuration; a corresponding compound of formula (III e) wherein $Y_1$ and $Y_3$ each represent hydroxy and $Y_2$ is hydrogen, and $Y_1$ and $Y_3$ forming a syn-diol configuration; is etherified by treatment, for example, with a compound of formula Hal-Alk-Hal for example, in the presence of a base.

Step (c):

Step (c) is carried out in the presence of a base, such as an alkane alkalimetal, especially butyl lithium, or a hydride, e.g. sodium hydride, or an alkali metal carbonate, especially $K_2CO_3$ or $Cs_2CO_3$, or a bulky amine, such as 1,5-diazabicyclo[4.3.0]non-5-ene (DBN) and 1,8-diaza-bicyclo[5.4.0]undec-7-ene (DBU), especially DBU in the presence of Lithium chloride, or an alkali metal hydroxide, especially KOH. The formation of a compound of formula (III g) is carried out in an inert solvent, such as tetrahydrofuran, or in protic solvent such as an alcohol, preferably isopropanol or ethanol, and in a temperature range from, for example, from −78° C., to the boiling point of the solvent, preferably from room temperature to 45° C., depending on the base and solvent used.

Preferred compounds of formula (III d) are those wherein Y represent a group of formula ($X_4$O)($X_5$O)P(=O)— and $X_4$ and $X_5$, in each case are especially, $C_1$-$C_4$alkyl, preferably methyl or ethyl.

Step (d):

For the manufacture of a compound of formula (III h), a compound of formula (III g), wherein one of $Y_1$ and $Y_3$ is protected hydroxy and the other is hydroxy or both of $Y_1$ and $Y_3$ is protected hydroxy and, in each case $Y_2$ is hydrogen; and $Y_1$ and $Y_3$ are forming the syn configuration; or $Y_1$ and $Y_3$ together represent —O-Alk-O— and Alk being $C_1$-$C_7$alkylidene and $Y_1$ and $Y_3$ are forming the syn configuration; and $Y_2$ is hydrogen; is used as starting material and the protection hydroxy group(s) is removed or the —O-Alk-O— group is split by treatment, for example, with a strong acid, such as a mineral acid, e.g. a hydrohalic acid, especially HCl, or a phosphoric acid, especially $H_3PO_4$.

If protected hydroxy is a corresponding silyloxy group, it will be split off with a fluoride salt e.g. tetrabutylammonium-fluoride, or with an acid, such as a mineral acid, e.g. a hydrohalic acid, or a phosphoric acid, especially $H_3PO_4$. The hydroxy protection group is split off in an inert solvent, such as a nitril, preferably acetonitril, and in a temperature range from, for example, from −78° C., to the boiling point of the solvent, preferably in a range of 0° to 50° C.

The preferred hydroxy protection group is the tert-butyl-dimethyl-silanyl-oxy group that is split off by using a mineral acid, e.g. $H_2SO_4$, HF, $H_3PO_4$, especially HCl.

Step (e):

For the manufacture of a compound of formula (III h), a compound of formula (III g), wherein $Y_1$ and $Y_2$ together form the oxo group and $Y_3$ is protected hydroxy; is used as starting material and the protection group of $Y_3$ is removed, for example, by treatment with a strong acid, such as a mineral acid, e.g. a hydrohalic acid, or a phosphoric acid, especially $H_3PO_4$.

If protected hydroxy is a corresponding silyloxy group, it will be split off with a fluoride salt e.g. tetrabutylammonium-fluoride, or with an acid, such as a mineral acid, e.g. a hydrohalic acid, or a phosphoric acid, especially $H_3PO_4$. The hydroxy protection group is split off in an inert solvent, such as a nitril, preferably acetonitril, and in a temperature range from, for example, from −78° C., to the boiling point of the solvent, preferably in a range of 0° to 50° C.

The preferred hydroxy protection group is the tert-butyl-dimethyl-silanyl-oxy group that is split off by using a mineral acid, e.g. $H_2SO_4$, HF, $H_3PO_4$, especially HCl.

The resulting compound of formula (III g), wherein $Y_1$ and $Y_2$ together form the oxo group and $Y_3$ is hydroxy, is reduced with a suitable reduction agent, for example, by catalytic hydrogenation in the presence of a hydrogenation catalyst, for example, a Ruthenium catalyst, such as (Ru (cod)(nu-3-(2-methylally))2, by reduction with a hydride, for example, a hydride which, if desired, may be complex, such as a hydride formed from an element of the 1st and 3rd main groups of the periodic table of the elements, for example borohydride or aluminohydride, for example lithium borohydride, lithium aluminium hydride, diisobutylaluminium hydride (an additional reduction step using alkali metal cyanoborohydride, such as sodium cyanoborohydride, may be necessary), and also diborane.

A preferred reduction agent is, for example, a hydride, for example, an alkalimetal borohydrid, especially sodium borohydride, preferably in the presence of a di-$C_1$-$C_7$alkyl-$C_1$-$C_7$alkoxy-borane, most preferably diethyl-methoxy-borane.

The reduction is carried out in an inert solvent, such as an ether, preferably tetrahydrofuran, in the presence of a protic solvent, such as an alcohol, especially methanol, and at low temperatures, for example, from −78° to 0° C., preferably at −78° C. To split a corresponding boronic ester the reaction mixture is then oxidized with an oxidizing agent, such as a peroxide, especially, hydrogen peroxide. The oxidation is carried out in an inert solvent, such as a nitrile, preferably acetonitrile, and in a temperature range from, for example, from 0° C., to the boiling point of the solvent, preferably in a range of 20° to 50° C.

Step (f):

The hydrolysation step (f) is carried out, for example, by treating the amide of formula (III g) with a strong base, such as an alkali metal hydroxide, preferably NaOH, or with $Ca(OH)_2$ and acidifying the resulting reaction mixture.

Step (g):

The isolation step (g) of a compound of formula (I) is carried out according to conventional isolation methods, such as by crystallizing the resulting compound of formula (I) from the reaction mixture or by chromatography of the reaction mixture.

The starting material of formula (III c) can be prepared, for example, by esterification or amidation of a compound of formula

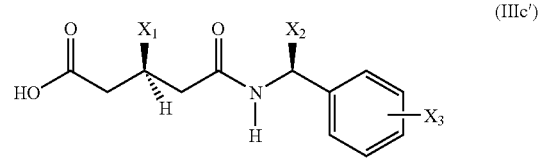

(IIIc')

in a method known per se.

The present invention furthermore relates to a process for the manufacture of a compound of formula

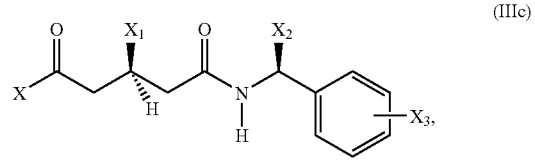

(IIIc)

wherein X is N—$C_1$-$C_7$alkyl-N—$C_1$-$C_7$alkoxy-amino, preferably, N-methyl-N-methoxy-amino, especially of formula

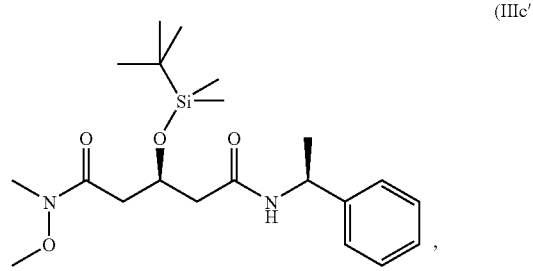

(IIIc' said process comprising reacting a compound of formula

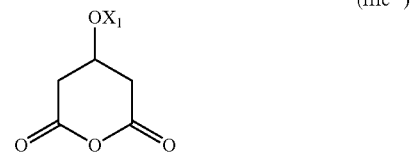

(IIIc''')

wherein $X_1$ is protected hydroxy, especially tert-butyl-dimethylsilyloxy, especially

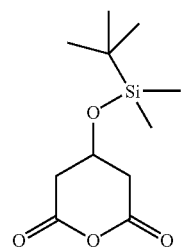

(cf. Compound (1)), with a compound of formula

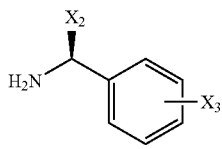

wherein X$_2$ and X$_3$ have the meanings given above, in the presence of a hindered amine or prefarably in the presence of at least two equivalents of 1-phenethylamine given above, and subsequent amidation with N—C$_1$-C$_7$alkyl-N—C$_1$-C$_7$-alkoxy-amine, especially with N-methyl-N-methoxy-amine.

A hindered amine is, for example, N—C$_1$-C$_7$alkyl-N—C$_1$-C$_7$alkoxy-amino, especially N-ethyl-diisopropyl-amine.

The process for the manufacture of the starting material of formula (III c), especially of a compound of formula (III c) wherein X is N—C$_1$-C$_7$alkyl-N—C$_1$-C$_7$-alkoxy-amino, especially N-methyl-N-methoxy-amino, is likewise a subject matter of the present invention. A significant higher selectivity can be achieved.

A compound of formula (III c) wherein X is N—C$_1$-C$_7$alkyl-N—C$_1$-C$_7$-alkoxy-amino, especially N-methyl-N-methoxy-amino, is likewise a subject matter of the present invention.

Furthermore, the present invention also relates to reaction step (a), especially when using a compound of formula (III c), wherein X is preferably N—C$_1$-C$_7$alkyl-N—C$_1$-C$_7$-alkoxy-amino, most preferably N-methyl-N-methoxy-amino. When applying this method, no substantial β-elimination of the protected hydroxy group X$_1$ is oberserved, especially in view of the presence of the phenyl-ethyl amide that is stabilising the protected hydroxy group preventing β-elimination and resulting in high selectivity for the substitution reaction.

When corresponding diesters were used, it is known from the literature that β-elimination occurs as side reaction and selectivity is significantly lower.

Furthermore, the present invention also relates to reaction step (b), especially when using a compound of formula (III c), wherein X is preferably N—C$_1$-C$_7$alkyl-N—C$_1$-C$_7$-alkoxy-amino, most preferably N-methyl-N-methoxy-amino. Here likewise, no β-elimination has been observed and a signicant selectivity of the reaction can be achieved.

The present invention furthermore relates to corresponding compounds of formula (III d), especially those wherein X$_1$ is silyloxy, preferably tert-butyl-dimethyl-silyloxy.

The present invention furthermore relates to corresponding compounds of formula (III e), especially those wherein Y$_3$ is silyloxy, preferably tert-butyl-dimethyl-silyloxy.

Furthermore, the present invention also relates to reaction step (c), especially when using a compound of formula (III e), wherein Y$_3$ is silyloxy, preferably tert-butyl-dimethyl-silyloxy. Here likewise, no β-elimination has been observed and a signicant selectivity of the reaction can be achieved.

The compound of formula (III e) is preferably represented by following formulae

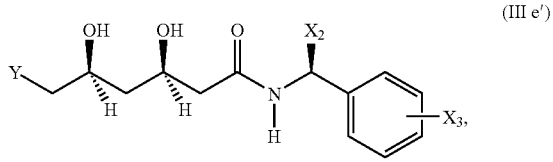

wherein Alk$_1$ represents preferably 1-methyl-1,1-ethylidene.

The present invention likewise relates to a compound of formulae (III e'), (III e'') and (III e''') and the manufacture thereof.

The present invention furthermore relates to corresponding compounds of formula (III g), especially those wherein Y$_3$ is silyloxy, preferably tert-butyl-dimethyl-silyloxy.

The present invention likewise relates to the novel compound as described in the Working Examples part.

The present invention likewise relates to the concrete products directly obtained by the process sequence or by the single process steps, especially the corresponding products that are in an essentially enantiomerically pure form.

The conversion of an acid of formula (I) into a salt is carried out in a manner known per se. Thus, for example, a salt with a base of compounds of the formula I is obtained by treating with a base. Salts can be converted into the free compounds in a customary manner, and salts with a base can be converted, for example, by treating with a suitable acid agent to the free acid.

The conversion of an acid of formula (I) into a corresponding lactone of formula (I a) or (I b), respectively, is carried out in the presence of an acid, preferably a mineral acid, in a suitable, e.g. protic or aproctic, solvent, such as ethanol or acetonitrile. Depending on the acid, the conversion is carried out in a temperature range, for example, from −78° to the boiling point of the solvent. Most preferably, H$_3$PO$_4$ in acetonitrile at 60° C. is used.

The conversion of a lactone of formula (I a) or (I b), respectively, into a salt of the acid of formula (I) is carried out, for example, in mixture of a protic solvent, e.g. ethanol, and water, by using an alkalimetall hydroxide, such as LiOH, NaOH or Ca(OH)$_2$. Alternatively, the lactone can be hydrolysed by using an alkalimetall hydroxide, such as LiOH, NaOH and the resulting salt can be converted into the calcium salt of the acid of pitavastatin by addition of an aqueous solution of CaCl$_2$ in water.

A variant to the process according to the present invention comprises the direct formation of a lactone of a compound of formula (I). The formation of said lactone can be carried out by treating a compound of formula (III h) with an acid, such as a mineral acid, preferable with H$_3$PO$_4$.

The process for the manufacture of compounds of formula (I) and salts thereof can be, for example, illustrated by means of the following reaction scheme for the manufacture of pitavastatin:

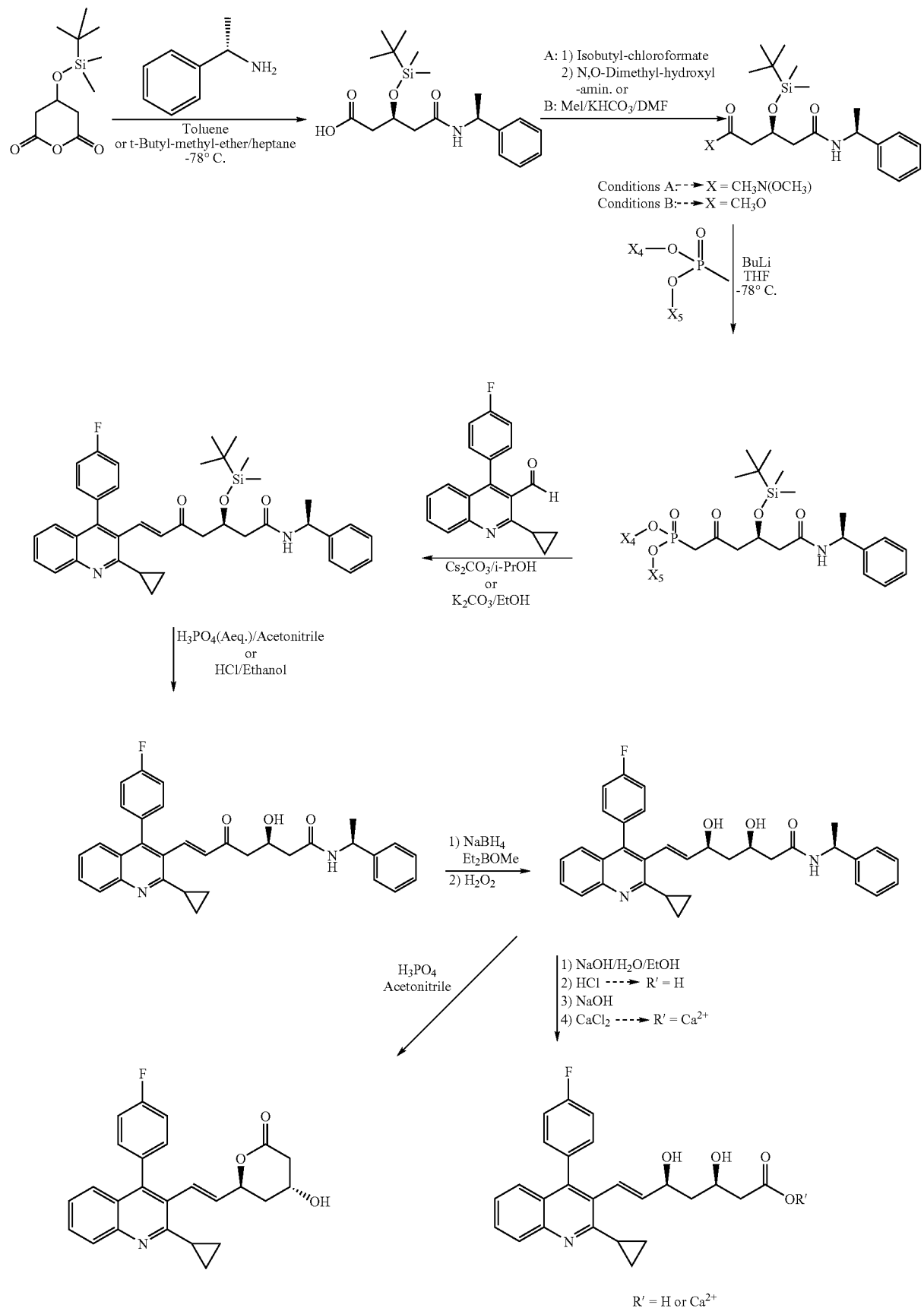

WORKING EXAMPLES

Manufacture of Starting Material

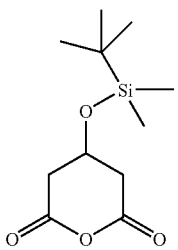

3-(tert-Butyidimethylsilyloxy)-glutaric anhydride can be purchased from Aldrich.

3-(tert-Butyldimethylsilyloxy)-glutaric anhydride can be prepared as follows:

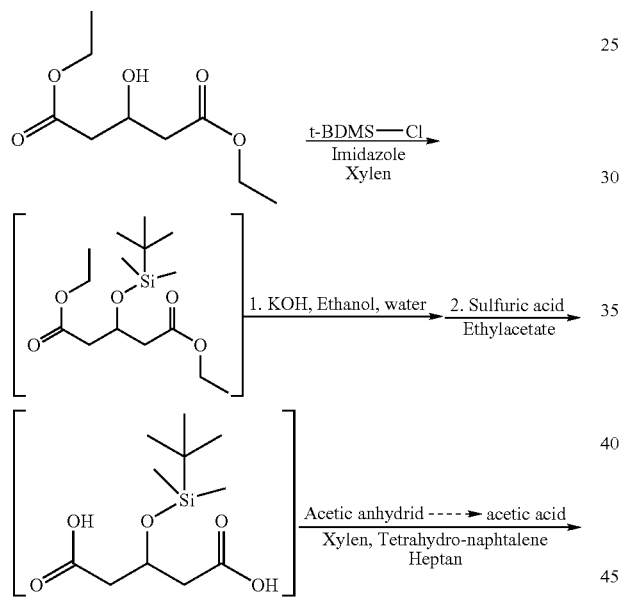

A 4-necked, round bottomed flask, equipped with a mechanical stirrer, digital thermometer, nitrogen inlet-outlet and a condenser is charged with 3-hydroxyglutaric acid diethyl ester (107.5 g, 0.5 mole), imidazole (44.2 g 0.6 mole) and xylene (200 mL). The resulting mixture is heated to 70-80° C. and t-butyidimethylchlorsilane (84.1 g 0.55 mole) dissolved in xylene (100 mL) are added drop wise over 30-40 minutes. Stirring is then prolonged for 3 to 6 hours at 70-80° C. Afterwards the emulsion is cooled to room temperature and water (200 mL) is added. The lower aqueous phase is removed and the remaining organic phase washed again with water (100 mL). Then, ethanol (95%, 200 mL) and a solution of potassium hydroxide (119.8 g a 49.2%, 1.05 mole) are added to the organic phase. Stirring is maintained for about 10-20 hours at 15-25° C. Then water (1200 mL) and ethyl acetate (300 mL) are added to the slurry. The resulting emulsion is cooled to 0-15° C. and sulfuric acid (about 230 ml 20% solution in water) is added carefully at 0-15° C. to end up with a pH value of 3.0-3.5 (acidification has to be done without interruption since the intermediate mono potassium salt is very labile and may decompose). The emulsion is then warm up to 15-20° C. and the lower aqueous layer removed. The remaining organic phase is washed with water (200 mL). Tetrahydronaphtalene (100 mL) and water (200 mL) are added. After a short stirring the aqueous phase is removed again, and the remaining organic phase concentrated under vacuo to ½ (200-60 mbar) at 60-70° C. Then acetic anhydride (103.5 g, 1.0 mole) is added over 20-40 minute at 55-65° C. and the solution stirred for 2-4 hours. The solution is concentrated again under vacuo jacket 80° C., 100-20 mbar). Then heptan (600 mL) is added slowly by 30-40° C. to allow the product to crystallise. The slurry is cooled to −15° C., stirred for about 1 hour, and crystals are collected, washed with heptane (100 mL) and dried under vacuo (60° C., 10-20 mbar). The pink sand like crystals, M.p. 58-68° C. (partial) then 80-82° C. are used as it for the next step.

Compound (2)

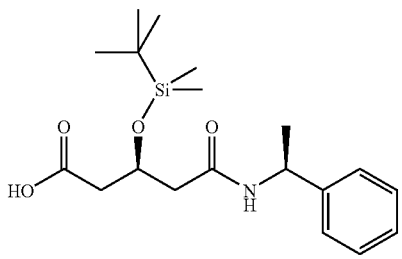

(3S,1'S)-3-[(tert-Butyidimethylsilyl)oxy]-5-[(1-phenyl-ethyl)amino]-5-oxopentanoic acid can be prepared according to a procedure as described in Donald. S. Karanewsky, Mary F. Malley and Jack Z. Gougoutas, J. Org. Chem. 1991, 56, 3744-3747, the corresponding method is herewith incorporated into the present application by reference.

The procedure of Karanewsky et al. can be improved to achieve higher diastereoselectivities and higher yields of the desired diastereomer by replacement of triethyl-amine with a more hindered base, especially N-ethyl-diisopropyl-amine. Said replacement results in better ratios and yields of the desired diastereomer in comparison to the undesired one. When triethyl-amine is replaced with (S)-(−)-1-phenethylamine as a base, the desired diastereomer is obtained in higher yield than described by Karanewsky et al. as well. This means that at least 2 moles of (S)-(−)-1-phenethylamine are used, one mole as substrate and at least one mole as base. Best ratios and yields of the desired diastereomer are achieved, if a second molequivalent of (S)-(−)-1-phenethylamine is used as a base, instead of the tertiary amine. (3S,1'S)-3-[(tert-butyldimethylsilyl)oxy]-5-[(1-phenyl-ethyl)amino]-5-oxopentanoic acid prepared by these procedures has usually >98% de and >98% ee.

An improved method is decribed below:

A 4-necked, round bottomed flask, equipped with a mechanical stirrer, digital thermometer, nitrogen inlet-outlet and a condenser is charged with the anhydride (compound 1) (30 g, 0.123 mol) and t-butylmethyl ether (210 mL) and heptan (120 mL). The clear solution is cooled down to −78°

C. making a slurry. (S)-(−)-1-phenethylamine (31.3 g, 0.258 mol, 99.6% ee) in heptan (120 mL) is added slowly over 60-90 minutes at −78/−75° C. The clear viscous solution is stirred for about 2 hours. Then temperature is after then raised to 20-25° C. Water (100 mL) is added followed by phosphoric acid (about 100 ml 20% solution in water) in such a way to keep the temperature between 30-35° C. and to end with a pH value of 2.5-3.5. The mixture is then brought to reflux (jacket 70° C.) and stirred for about 30 minutes. Then it is cooled down to 0-5° C. and filtered to recover the white crystals which are washed with a mixture of heptan/water 1:1 (80 mL) followed by dilute ethanol (20% in water, 100 mL). The crystals obtained are dried under vacuo (50-60° C., 10-20 mbar). M.p. 170-172° C.

(3S,1'S)-3-[(tert-butyldimethylsilyl)oxy]-5-[(1-phenyl-ethyl)amino]-5-oxopentanoic acid prepared by this procedure has usually >98% de and >98% ee.

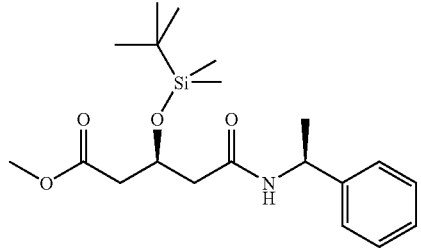

Compound (3)

(3S,1'S)-3-[(tert-Butyldimethylsilyl)oxy]-5-[(1-phenyl-ethyl)amino]-5-oxopentanoic acid methyl ester can be prepared according to the procedure of Karanewsky et al., cited above.

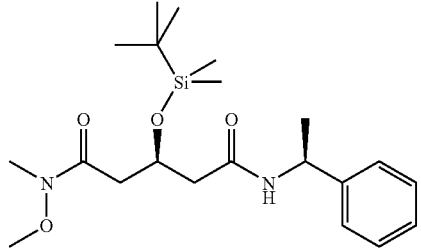

Compound (4)

(S)-3-(tert-Butyl-dimethyl-silanyloxy)-pentanedioic acid methoxy-methyl-amide-((S)-1-phenyl-ethyl)amide can be prepared as follows:

A 4-necked, round bottomed flask, equipped with a mechanical stirrer, digital thermometer, nitrogen inlet-outlet and a condenser is charged with the acid (compound 2) (10 g, 27.36 mmol) and dichloromethane (200 mL). N-Methyl-morpholine (6.03 mL, 54.71 mmol) is added under stirring at room temperature, to obtain a clear solution. The reaction mixture is cooled down to −20° C. Isobutyl-chloroformate (3.76 mL, ca. 95% w/w purity, 27.36 mmol) is added to the reaction mixture at −15 to −20° C. The mixture is stirred for 15 min. at −15 to −20° C. and is treated with N,O-dimethyl-hydroxylamine hydrochloride (2.695 g, 27.36 mmol). Stirring is continued for 1 h and the reaction mixture is allowed to warm-up to room temperature. The reaction mixture is stirred for 1 h at room temperature and is treated with water (200 ml) to obtain a biphasic solution. The layers are separated and the water layer is extracted with dichloromethane (2×200 mL). The organic layer is washed with brine (200 mL), dried over anhydrous MgSO$_4$ and the solvent is evaporated under reduced pressure to obtain crude (S)-3-(tert-butyl-dimethyl-silanyloxy)-pentanedioic acid methoxy-methyl-amide-((S)-1-phenyl-ethyl)amide. The crude product is recrystallized from hexanes to obtain pure (S)-3-(tert-butyl-dimethyl-silanyloxy)-pentanedioic acid methoxy-methyl-amide-((S)-1-phenyl-ethyl)amide. M.p. 69.6-70.1° C.; $[\alpha]_D^{25}$=−27° (CHCl$_3$, c=1); MS (ES+, m/z): 431 ([M+Na]$^+$, 100%); IR(KBr): Strong absorbtions at 3304, 1666, 1630, 1541 and 831 cm$^{-1}$.

Example 1 a)

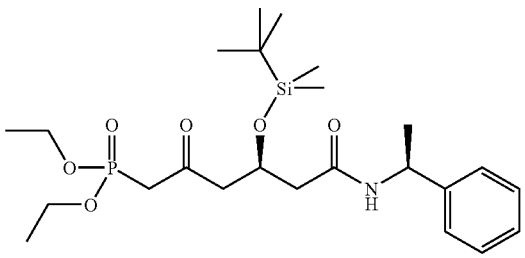

[(R)-4-(tert-Butyl-dimethyl-silanyloxy)-2-oxo-5-((S)-1-phenyl-ethylcarbamoyl)-pentyl]-phosphonic acid diethyl ester can be prepared as follows:

A 4-necked, round bottomed flask, equipped with a mechanical stirrer, digital thermometer, nitrogen inlet-outlet and a condenser is charged with methanphosphonic acid diethyl ester (4.65 g, 30.59 mmol) and tetrahydrofuran (11 mL). The solution is cooled down to −78° C. and butyl-lithium (15.3 mL of a 1.6 M solution in hexane, 24.47 mmol) is added. After stirring for additional 60 min at −78° C., a solution of (S)-3-(tert-butyl-dimethyl-silanyloxy)-pentanedioic acid methoxy-methyl-amide-((S)-1-phenyl-ethyl)amide (2.5 g) in tetrahydrofuran (10 mL) is added to the reaction mixture while maintaining the temperature at −78° C. Stirring is continued for 1 h at this temperature and the reaction is quenched by slow addition of a solution of acetic acid (1.84 g) in tetrahydrofuran (1.25 ml) at −78° C. The reaction mixture is then allowed to warm up to room temperature and poured onto ethyl acetate (125 mL) and brine (125 mL). The biphasic mixture is stirred for 10 min and the organic layer is separated. The water layer is extracted with ethyl acetate. The organic layers are combined, washed with water, dried over anhydrous magnesium sulfate and the solvent is evaporated in vacuo to obtain the crude [(R)-4-(tert-Butyl-dimethyl-silanyloxy)-2-oxo-5-((S)-1-phenyl-ethylcarbamoyl)-pentyl-phosphonic acid diethyl ester as a viscous oil. The crude product is purified by column chromatography with ethyl acetate/hexane (1:1) as eluent to obtain [(R)-4-(tert-Butyl-dimethyl-silanyloxy)-2-oxo-5-((S)-1-phenyl-ethylcarbamoyl)-pentyl]-phosphonic acid diethyl ester as a highly viscous oil. $[\alpha]_D^{20}$=−40.2° (CHCl$_3$, c=1); MS (ES+, m/z): 522 ([M+Na]$^+$, 100%); IR(Film): strong absorbtions at 3297, 2930, 1717, 1652, 1542, 1254, 1026, 837 cm$^{-1}$.

Alternatively, [(R)-4-(tert-Butyl-dimethyl-silanyloxy)-2-oxo-5((S)-1-phenyl-ethylcarbamoyl)-pentyl]-phosphonic acid diethyl ester can be also prepared using the methyl ester of (3S,1'S)-3-[(tert-butyldimethylsilyl)oxy]-5-[(1-phenyl-ethyl)amino]-5-oxopentanoic acid as starting material instead of (S)-3-(tert-butyl-dimethyl-silanyloxy)-pentanedioic acid methoxy-methyl-amide-((S)-1-phenyl-ethyl)amide applying the above described method.

b)

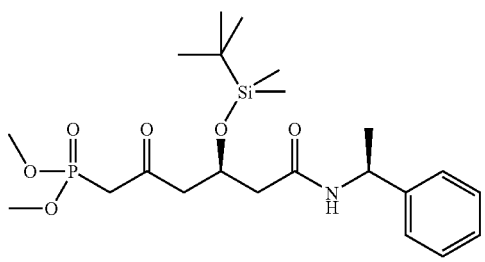

[(R)-4-(tert-Butyl-dimethyl-silanyloxy)-2-oxo-5-((S)-1-phenyl-ethylcarbamoyl)-pentyl]-phosphonic acid dimethyl ester can be prepared as follows:

[(R)-4-(tert-Butyl-dimethyl-silanyloxy)-2-oxo-5-((S)-1-phenyl-ethylcarbamoyl)-pentyl]-phosphonic acid dimethyl ester is prepared by applying the procedure as described for [(R)-4-(tert-butyl-dimethyl-silanyloxy)-2-oxo-5-((S)-1-phenyl-ethylcarbamoyl)-pentyl]-phosphonic acid diethyl ester.

[(R)-4-(tert-Butyl-dimethyl-silanyloxy)-2-oxo-5((S)-1-phenyl-ethylcarbamoyl)-pentyl]-phosphonic acid dimethyl ester is obtained as a highly viscous oil, which solidified on storage in the refrigerator. $[\alpha]_D^{20}=-37.7°$ (CHCl$_3$, c=1); MS (ES+, m/z): 494 ([M+Na]$^+$, 100%); IR(Film): strong absorbtions at 3299, 2955, 2929, 2855, 1717, 1651, 1542, 1256, 1035, 838, 779, 701 cm$^{-1}$.

c)

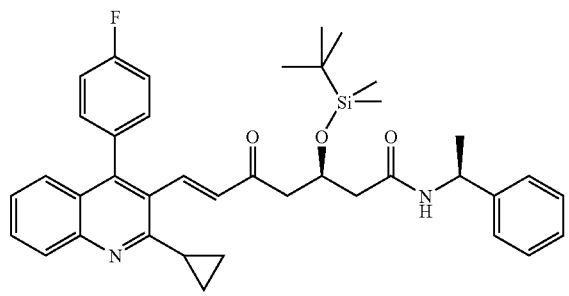

(E)-(R)-3-(tert-Butyl-dimethyl-silanyloxy)-7-[2-cyclopropyl-4-(4-fluoro-phenyl)-quinolin-3-yl]-5-oxo-hept-6-enoic acid ((S)-1-phenyl-ethyl)-amide can be prepared as follows:

[(R)-4-(tert-Butyl-dimethyl-silanyloxy)-2-oxo-5((S)-1-phenyl-ethylcarbamoyl)-pentyl]-phosphonic acid diethyl ester (3 g, 6 mmol) is placed in a 4-necked, round bottomed flask, equipped with a mechanical stirrer, digital thermometer, nitrogen inlet-outlet and a condenser. Isopropanol (12 mL) is added to obtain a solution. Caesium carbonate (1.96 g, 6 mmol) is added, followed by the addition of the 2-cyclopropyl-4-(4-fluoro-phenyl)-quinolin-3-yl]-3-carbaldehyde (1.75 g, 6 mmol). The reaction mixture is diluted with isopropanol (6 ml) and stirred overnight at room temperature. Then, the reaction is quenched by addition of an aqueous citric acid solution (60 mL) and the aqueous mixture is extracted twice with tert-butyl-methylether (2×120 mL). The organic layers are combined, washed with water (120 mL), dried over anhydrous magnesium sulfate and the solvent is evaporated under reduced pressure to obtain the crude product as a brownish-yellow foam. The crude product is purified by column chromatography on silica gel, with hexane/ethyl acetate (7:3) as eluent to obtain (E)-(R)-3-(tert-Butyl-dimethyl-silanyloxy)-7-[2-cyclopropyl-4-(4-fluoro-phenyl)-quinolin-3-yl]-5-oxo-hept-6-enoic acid ((S)-1-phenyl-ethyl)-amide as a light-yellow solid foam. $[\alpha]_D^{20}=-28.8°$ (CHCl$_3$, c=1); MS (ES+, m/z): 659 ([M+Na]$^+$, 100%); IR(KBr): Strong absorbtions at 1647, 1605, 1540, 1513, 1253, 1223, 1094, 1066, 837, 778, 763, 6999 cm$^{-1}$.

Alternatively, (E)-(R)-3-(tert-Butyl-dimethyl-silanyloxy)-7-[2-cyclopropyl-4-(4-fluoro-phenyl)-quinolin-3-yl]-5-oxo-hept-6-enoic acid ((S)-1-phenyl-ethyl)-amide can be prepared from [(R)-4-(tert-Butyl-dimethyl-silanyloxy)-2-oxo-5-((S)-1-phenyl-ethylcarbamoyl)-pentyl]-phosphonic acid dimethyl ester e.g. by using the following procedure:

[(R)-4-(tert-Butyldimethyl-silanyloxy)-2-oxo-5-((S)-1-phenyl-ethylcarbamoyl)-pentyl]-phosphonic acid dimethyl ester (424.9 g, 910 mmol) is placed in a 4-necked, round bottomed flask, equipped with a mechanical stirrer, digital thermometer, nitrogen inlet-outlet and a condenser. Ethanol (950 mL) is added to obtain a solution. The solution is cooled to 0-4° C. in an ice bath. Finely powdered potassium carbonate (119.8 g, 858.1 mmol) is added, followed by the addition of the 2-cyclopropyl-4-(4-fluoro-phenyl)-quinolin-3-yl]-3-carbaldehyde (250 g, 858.1 mmol). The reaction mixture is diluted with ethanol (950 ml) and allowed to warm up to room temperature. After stirring for 30 min at room temperature, the reaction mixture was heated to 40-45° C. and stirred at this temperature for 48 hours. The reaction is then quenched by pouring onto a 5% solution of aqueous citric acid (1800 mL). The reaction mixture is transferred into a separation funnel and is extracted with t-butyl-methylether (3500 mL). The layers are separated and the organic layer is washed with water (3500 mL) and brine (3500 mL). The water layers are extracted again with t-butyl-methylether (5500 mL) and the organic layers are combined. The organic layer is dried over magnesium sulfate (70 g) and the solvent is evaporated in vacuo to obtain a braun honey-like crude product, which can be purified by column chromatography as described above to obtain pure (E)-(R)-3-(tert-Butyl-dimethyl-silanyloxy)-7-[2-cyclopropyl-4-(4-fluoro-phenyl)-quinolin-3-yl]-5-oxo-hept-6-enoic acid ((S)-1-phenyl-ethyl)-amide. Alternatively, the crude product can be used for the next step without further purification.

d)

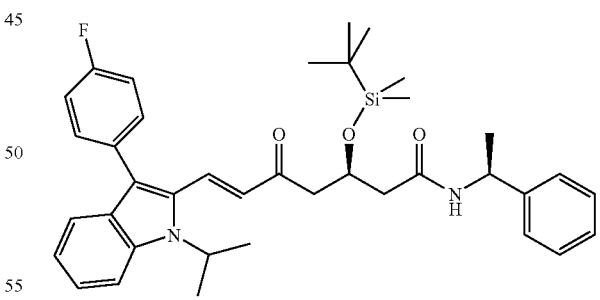

(E)-(R)-3-(tert-Butyl-dimethyl-silanyloxy)-7-[3-(4-fluoro-phenyl)-1-isopropyl-1H-indol-2-yl]-5-oxo-hept-6-enoic acid ((S)-1-phenyl-ethyl)-amide can be prepared from 3-(4-Fluoro-phenyl)-1-isopropyl-1H-indole-2-carbaldehyde and [(R)-4-(tert-Butyl-dimethyl-silanyloxy)-2-oxo-5-((S)-1-phenyl-ethylcarbamoyl)-pentyl]-phosphonic acid dimethyl ester according to the procedure described above. After chromatography on silica gel with n-hexanes/ethyl acetate (7:3) as eluent, (E)-(R)-3-(tert-Butyl-dimethyl-silanyloxy)-7-[3-(4-fluoro-phenyl)-1-isopropyl-1H-indol-2-yl]-5-oxo-hept-6-enoic acid ((S)-1-phenyl-ethyl)-amide is obtained as a yellow foam. $R_f$=0.65 (TLC on silicagel with ethyl acetate/hexanes 9:1 as eluent). $[\alpha]_D^{20}$=−40.1° (MeOH, c=1); MS (ES+, m/z): 649 (100%, M+Na+); IR(KBr): characteristic signals at 3309 (broad), 3062, 2954, 2929, 2884, 2855, 1652, 1591, 1540, 1496, 1453, 1371, 1339, 1251, 1222, 1156, 1138, 1093, 1015, 970, 837, 778, 743, 699, 565 cm$^{-1}$; Microanalysis: calculated (found) for $C_{38}H_{47}FN_2O_3Si$: 72.81 (72.69) % C, 7.56 (7.73) % H, 4.47 (4.61) % N, 3.03 (2.99) % F, 4.48 (4.36) % Si.

e)

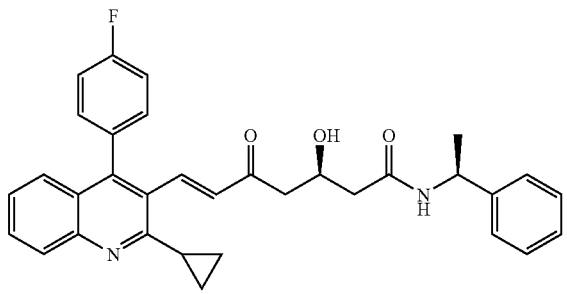

(E)-(R)-7-[2-cyclopropyl-4-(4-fluoro-phenyl)-quinolin-3-yl]-3-hydroxy-5-oxo-hept-6-enole acid ((S)-1-phenyl-ethyl)-amide can be prepared as follows:

(E)-(R)-3-(tert-Butyl-dimethyl-silanyloxy)-7-[2-cyclopropyl-4-(4-fluoro-phenyl)-quinolin-3-yl]-5-oxo-hept-6-enoic acid ((S)-1-phenyl-ethyl)-amide (2.0 g, 3.14 mmol) is placed in a 4-necked, round bottomed flask, equipped with a mechanical stirrer, digital thermometer, nitrogen inlet-outlet and a condenser. Acetonitril (30 mL) is added and the mixture is stirred to obtain a solution. A preformed solution of phosphoric acid (10 mL of a 1M solution in water) is added and the reaction mixture is heated to 45° C. Stirring is continued for 29 h at this temperature. Then, the reaction mixture is poured onto aqueous saturated NaHCO$_3$ solution (65 mL) and the mixture is extracted with ethyl acetate (2×70 mL). The organic layers are washed with brine, dried over anhydrous magnesium sulfate and the solvent is evaporated under reduced pressure to obtain a solid foam. The crude product is used without further purification for the next step.

An analytical sample of the crude product is purified by column chromatography on silica gel using ethyl acetate as eluent and subsequently crystallised from tert-butyl-methylether/hexane, to obtain pure (E)-(R)-7-[2-cyclopropyl-4-(4-fluoro-phenyl)-quinolin-3-yl]-3-hydroxy-5-oxo-hept-6-enoic acid ((S)-1-phenyl-ethyl)-amide. M.p. 150-151° C.; $[\alpha]_D^{20}$=−26.9° (CHCl$_3$, c=1); MS (ES+, m/z): 545 ([M+Na]+), 523 (MH+, 100%); IR (KBr): Strong absorptions at 3344, 1693, 1631, 1603, 1549, 1513, 1488, 1409, 1344, 1219, 1055, 1030, 768, 697 cm$^{-1}$; Microanalysis: calculated (found) for $C_{33}H_{31}FN_2O_3$: 75.84 (75.74) % C, 5.98 (6.13) % H, 5.36 (5.39) % N, 3.64 (3.63) % F.

Alternatively, (E)-(R)-7-[2-cyclopropyl-4-(4-fluoro-phenyl)-quinolin-3-yl]-3-hydroxy-5-oxo-hept-6-enoic acid ((S)-1-phenyl-ethyl)-amide can be prepared using hydrochloric acid for deprotection according to the following procedure:

Crude (E)-(R)-3-(tert-Butyl-dimethyl-silanyloxy)-7-[2-cyclopropyl-4-(4-fluoro-phenyl)-quinolin-3-yl]-5-oxo-hept-6-enoic acid ((S)-1-phenyl-ethyl)-amide (655.1 g) from example c) is placed in a 4-necked, round bottomed flask, equipped with a mechanical stirrer, digital thermometer, nitrogen inlet-outlet and a condenser. Ethanol (2400 mL) is added to obtain a solution. The solution is cooled to 0-4° C. and hydrochloric acid (2M aqueous solution, 657.1 g, 1276 mmol) is added dropwise at this temperature. The reaction mixture is warmed up to 25° C. and stirred at this temperature for additional 4 hours for completion of the deprotection. The reaction mixture is then poured onto an aqueous solution of sodium bicarbonate (7400 mL of a 2% solution) and extracted with ethyl acetate (5000 mL). The organic layer is washed with brine (1800 mL), the water layers are combined and extracted with ethyl acetate (2000 mL). The organic layers are combined, dried over magnesium sulfate and the solvent is evaporated in vacuo to obtain 561.2 g of a braun, honey-like crude product. The crude product is dissolved in toluene (860 mL) and n-hexane (1075 mL) is added. The mixture is heated at 60° C. for 2 hours and at 50° C. for 1 hour. n-Hexane (1075 mL) is added at 50° C. and the suspension is allowed to cool down to room temperature. Stirring is continued over night at room temperature and for additional 3 hours at 0° C. The solid product is isolated by filtration, the filter cake is washed with ice-cold n-hexane (502 mL) and dried in vacuo to obtain (E)-(R)-7-[2-cyclopropyl-4-(4-fluoro-phenyl)-quinolin-3-yl]-3-hydroxy-5-oxo-hept-6-enoic acid ((S)-1-phenyl-ethyl)-amide as a yellow powder.

f)

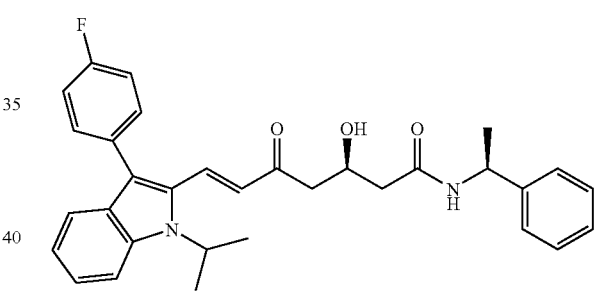

(E)-(R)-7-[3-(4-Fluoro-phenyl)-1-isopropyl-1H-indol-2-yl]-3-hydroxy-5-oxo-hept-6-enoic acid ((S)-1-phenyl-ethyl)-amide can be prepared from (E)-(R)-3-(tert-Butyl-dimethyl-silanyloxy)-7-[3-(4-fluoro-phenyl)-1-isopropyl-1H-indol-2-yl]-5-oxo-hept-6-enoic acid ((S)-1-phenyl-ethyl)-amide by deprotection with HCl in ethanol according to the procedure described above for the preparation of (E)-(R)-7-[2-cyclopropyl-4-(4-fluoro-phenyl)-quinolin-3-yl]-3-hydroxy-5-oxo-hept-6-enoic acid ((S)-1-phenyl-ethyl)-amide. Chromatography on silicagel with ethyl acetate/n-hexanes (9:1) as eluent affords (E)-(R)-7-[3-(4-Fluoro-phenyl)-1-isopropyl-1H-indol-2-yl]-3-hydroxy-5-oxo-hept-6-enoic acid ((S)-1-phenyl-ethyl)-amide as a yellow foam. $R_f$=0.30 (TLC on silicagel, ethyl acetate/hexanes 9:1 as eluent). $[\alpha]_D^{20}$=−35.5° (CH$_3$OH, c=1) MS (ES+, m/z): 535 ([MNa]+, 100%); IR (KBr): 3307 (broad), 3061, 2973, 2932, 1645, 1590, 1539, 1495, 1452, 1421, 1371, 1339, 1273, 1221, 1155, 1138, 1105, 1095, 1048, 1016, 973, 910, 839, 815, 744, 719, 700 cm$^{-1}$. Microanalysis: calculated (found) for $C_{32}H_{33}FN_2O_3$: 74.98 (74.20) % C, 6.49 (6.49) % H, 5.46 (5.49) % N, 3.71 (3.58) % F.

g)

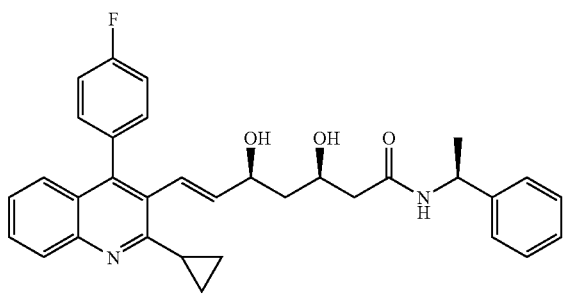

(E)-(3R,5S)-7-[2-Cyclopropyl-4-(4-fluoro-phenyl)quinolin-3-yl]-3,5-dihydroxy-hept-6-enoic acid ((S)-1-phenyl-ethyl)-amide can be prepared as follows:

A dry, 3-necked, round bottomed flask, equipped with a stirring bar, digital thermometer and argon inlet-outlet is charged with dry tetrahydrofuran (7.5 mL) and is cooled down to −78° C. Sodium borohydride (172.5 mg, 4.56 mmol) is added under an argon stream, followed by the addition of diethyl-methoxyborane (0.694 g of a 50% solution in tetrahydrofuran, 3.47 mmol) at −78° C. The mixture is stirred for 5 min at this temperature. Then, a solution of crude (E)-(R)-7-[2-cyclopropyl-4-(4-fluoro-phenyl)-quinolin-3-yl]-3-hydroxy-5-oxo-hept-6-enoic acid ((S)-1-phenyl-ethyl)-amide (1.84 g, 3.52 mMol) in dry tetrahydrofuran (1.8 mL) and dry methanol (2.2 mL) is added slowly during ca. 30 min at −78° C. and stirring is continued for another 1 h at this temperature. For work-up, the reaction mixture is poured onto a solution of sodium bicarbonate (0.383 g) in water (12 mL) and isopropyl acetate (30 mL) is added. The biphasic solution is stirred for 30 min at room temperature, until gas evolution is ceased. The layers are separated and the organic layer is washed with brine (2×30 mL). The solvent is evaporated in vacuo to obtain a dry, yellow solid. The solid is dissolved in isopropyl acetate (15 mL) and the solution is heated to 45-50° C. Hydrogen-peroxide (0.994 g of a 35% aqueous solution, 10.23 mmol) is slowly added at 45-50° C. and stirring is continued for additional 2 h. The reaction is quenched by addition of brine (15 mL) at 45-50° C. The biphasic mixture is stirred for 20 min at 45-50° C. and the layers are separated. The organic layer is treated with an aqueous solution of Na$_2$SO$_3$ (0.658 g in 15 mL water) at 45-50° C., the mixture is stirred for 5 min and the layers are separated. Finally, the organic layer is washed with aqueous, half-saturated NaCl solution (15 mL), dried over magnesium sulfate and the solvent is evaporated in vacuo to obtain the crude product as a yellowish solid foam.

Purification of the crude product by column chromatography on silica gel with ethyl acetate/hexane (9:1) as eluent gives (E)-(3R,5S)-7-[2-cyclopropyl-4-(4-fluoro-phenyl)quinolin-3-yl]-3,5-dihydroxy-hept-6-enoic acid ((S)-1-phenyl-ethyl)-amide, which can be crystallized from tert-butyl-methylether as follows: (E)-(3R,5S)-7-[2-cyclopropyl-4-(4-fluoro-phenyl)quinolin-3-yl]-3,5-dihydroxy-hept-6-enoic acid ((S)-1-phenyl-ethyl)-amide (1.197 g) is dissolved in tert-butyl-methylether (10 mL) and hexane fraction (4 mL) is added dropwise under stirring. The clear solution is treated with a suspension of a small portion of seed crystals and stirring is continued for an additional hour at room temperature. The suspension formed is cooled down to 0-5° C. and stirred for 2 h at this temperature. The product is isolated by filtration, washed with ice-cold hexane fraction (5 mL) and dried in vacuo at 40° C. to obtain crystalline (E)-(3R,5S)-7-[2-cyclopropyl-4-(4-fluoro-phenyl)quinolin-3-yl]-3,5-dihydroxy-hept-6-enoic acid ((S)-1-phenyl-ethyl)-amide. $^1$H-NMR and microanalysis indicated the presence of a ca. 1:1 solvate form of the crystals with tert-butyl-methylether. M.p.: melting range 57-76° C.; $[\alpha]_D^{20}$=−27.0° (CHCl$_3$, c=1); MS (ES+, m/z): 547 ([M+Na]$^+$), 525 (MH$^+$, 100%); IR(KBr): Strong absorptions at 3479, 3296, 2977, 1642, 1557, 1513, 1490, 1215, 1116, 1068, 763, 698 cm$^{-1}$; Microanalysis: calculated (found) for C$_{33}$H$_{33}$FN$_2$O$_3$+C$_5$H$_{12}$O: 74.48 (74.47) % C, 7.40 (7.30) % H, 4.57(4.64) % N, 3.10 (3.13) % F.

Alternatively, (E)-(R)-7-[2-cyclopropyl-4-(4-fluoro-phenyl)-quinolin-3-yl]-3-hydroxy-5-oxo-hept-6-enoic acid ((S)-1-phenyl-ethyl)-amide precipitated from toluene, can be converted to (E)-(3R,5S)-7-[2-Cyclopropyl-4-(4-fluoro-phenyl)quinolin-3-yl]-3,5-dihydroxy-hept-6-enoic acid ((S)-1-phenyl-ethyl)-amide also by the following procedure:

Sodium-borohydride (30.26 g) is placed in a dry 4-necked, round bottomed flask, equipped with a mechanical stirrer, digital thermometer, nitrogen inlet-outlet and a condenser. Dry tetrahydrofuran (1877 mL) is added and the suspension is cooled down to −78° C. A solution of diethyl-methoxyborane (54.85 g, 548.4 mmol) in tetrahydrofuran (54.85 g) is added during 15 min. at −78° C. and the reaction mixture is stirred for additional 5 min. at this temperature. A solution of (E)-(R)-7-[2-cyclopropyl-4-(4-fluoro-phenyl)-quinolin-3-yl]-3-hydroxy-5-oxo-hept-6-enoic acid ((S)-1-phenyl-ethyl)-amide (290.7 g, 556 mmol) in dry tetrahydrofuran (488 mL) and methanol (581 mL) is added slowly during 2.5 hours to the reaction mixture, maintaining the reaction temperature at −78° C. After stirring for additional one hour at −78° C., the reaction mixture is poured onto an ice-cold solution of sodium bicarbonate (92.15 g) in water (4610 mL). Isopropyl acetate (7346 mL) is added and the biphasic mixture is stirred, until two clear phases are formed. The organic layer is separated and the aqueous layer is extracted with isopropyl acetate (2×3150 mL). The organic layers are combined, washed with brine. (2×3150 mL) and the solvent is evaporated in vacuo to obtain a solid as a yellow foam. The solid is dissolved in isopropyl acetate (630 mL) and the solution is warmed up to 50° C. Hydrogen peroxide (174.02 g of a 35% aqueous solution, corresponding to 60.907 g hydrogen peroxide, 1790 mMol) is added over a time period of 45 min. at 50° C. and the reaction mixture is stirred for an additional hour at this temperature. The reaction is quenched by addition of brine (3980 mL) at 45-50° C. and diluted with isopropyl acetate (2390 mL). The biphasic mixture is stirred for 20 min at 45-50° C. and the layers are separated. The organic layer is treated with an aqueous solution of Na$_2$SO$_3$ (118 g in 2850 mL water) at 45-50° C., the mixture is stirred for 5 min and the layers are separated. Finally, the organic layer is washed with aqueous, half-saturated NaCl solution (2×2390 mL), dried over magnesium sulfate and the solvent is evaporated in vacuo to obtain the crude product (349 g) as a yellow solid foam. The crude product was dissolved in t-butyl-methyl ether (706 mL) and the solution was cooled down to 0° C. After stirring for 30 min. at 0° C., the formed suspension is warmed up to 30° C. and stirred for 15 min. at this temperature. The suspension is allowed to cool down to 25° C. and stirred over night at this temperature. Finally, the suspension is stirred for 2 hours at 0° C. and for 3 hours at −20° C. The product is isolated by filtration, washed with n-heptane (2×75 mL) and dried in vacuo at 40° C. to obtain crystalline (E)-(3R,5S)-7-[2-Cyclopropyl-4-(4-fluoro-phenyl)quinolin-3-yl]-3,5-dihydroxy-hept-6-enoic acid ((S)-1-phenyl-ethyl)-amide as a solvate with t-butyl-methyl ether. Melting range 58-69° C. According to HPLC, the crystals comprised 99.89% of the desired syn-(3R,5S)-product and 0.11% of the anti-(3R,5R)-epimer.

h)

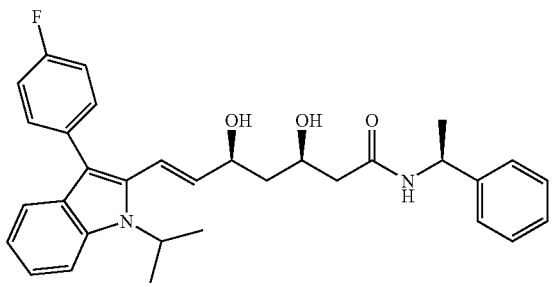

(E)-(3R,5S)-7-[3-(4-Fluoro-phenyl)-1-isopropyl-1H-indol-2-yl]-3,5-dihydroxy-hept-6-enoic acid ((S)-1-phenylethyl)-amide can be prepared from (E)-(R)-7-[3-(4-Fluoro-phenyl)-1-isopropyl-1H-indol-2-yl]-3-hydroxy-5-oxo-hept-6-enoic acid ((S)-1-phenyl-ethyl)-amide according to the procedures described above for the preparation of (E)-(3R,5S)-7-[2-Cyclopropyl-4-(4-fluoro-phenyl)quinolin-3-yl]-3,5-dihydroxy-hept-6-enoic acid ((S)-1-phenyl-ethyl)-amide. Chromatography on silicagel with ethyl acetate/hexanes (9:1) as eluent affords (E)-(3R,5S)-7-[3-(4-Fluoro-phenyl)-1-isopropyl-1H-indol-2-yl]-3,5-dihydroxy-hept-6-enoic acid ((S)-1-phenyl-ethyl)-amide as a light yellow foam. $R_f$=0.175 (TLC on silicagel, ethyl acetate/hexanes 9:1 as eluent). $[\alpha]_D^{20}$ =−16.7° ($CH_3OH$, c=1). MS (ES+, m/z): 537 ([M+Na]$^+$, 100%); IR(KBr): 3310 (broad), 3049, 2974, 2934, 2875, 1644, 1604, 1545, 1501, 1457, 1420, 1371, 1346, 1219, 1155, 1104, 1065, 1045, 1018, 970, 944, 837, 814, 742, 718, 700, 565.

i)

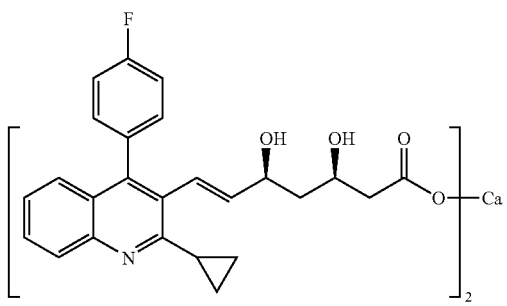

(E)-(3R,5S)-7-[2-Cyclopropyl-4-(4-fluoro-phenyl)-quinolin-3-yl]-3,5-dihydroxy-hept-6-enoic acid, calcium salt can be prepared as follows:

(E)-(3R,5S)-7-[2-Cyclopropyl-4-(4-fluoro-phenyl)quinolin-3-yl]-3,5-dihydroxy-hept-6-enoic acid ((S)-1-phenyl-ethyl)-amide (0.50 g, 0.95 mmol) is dissolved in ethanol (12.5 mL). Water (12.5 mL) and sodium hydroxide (5 mL of a 1M solution, 5 mmol) are added and the mixture is heated to ca. 80° C. in an oil bath. Stirring is continued for 18 h at ca. 80° C. The solvent is distilled under reduced pressure and the residue is dissolved in water (50 mL). The water solution is extracted twice with tert-butyl-methyl ether (2×50 mL). The aqueous layer is concentrated in vacuo to a final volume of ca. 25 mL. Water (25 mL) is added, followed by the addition of calcium chloride (0.049 g, 0.044 mmol) under stirring at 30-35° C.

Precipitation occurs. The suspension is allowed to cool down to room temperature. The suspension is stirred for 2 h at room temperature and for additional 2.5 h at 15° C. The precipitate is isolated by filtration and the filter-cake is washed with water (5 mL). The product is dried in vacuo to obtain the Calcium salt of pitavastatin as a white powder. The acid component of the salt is identical with the acid component of an authentic sample of (E)-(3R,5S)-7-[2-Cyclopropyl-4-(4-fluoro-phenyl)-quinolin-3-yl]-3,5-dihydroxy-hept-6-enoic acid, calcium salt (corresponding to the pitavastatin calcium salt) in IR and HPLC.

Alternatively, (E)-(3R,5S)-7-[2-Cyclopropyl-4-(4-fluoro-phenyl)-quinolin-3-yl]-3,5-dihydroxy-hept-6-enoic acid and its calcium salt respectively can be prepared as follows:

(E)-(3R,5S)-7-[2-Cyclopropyl-4-(4-fluoro-phenyl)quinolin-3-yl]-3,5-dihydroxy-hept-6-enoic acid ((S)-1-phenyl-ethyl)-amide (4.0 g, 6.53 mmol) is dissolved in ethanol (40 mL). Water (40 mL) and sodium hydroxide powder (2.64 g, 66 mmol) are added and the mixture is heated at 50-55° C. for 26 h, until an in-process control (HPLC) indicated complete conversion. Hydrochloric acid (59 mL of a 1M solution, 59 mmol) is added slowly over a time period of 15 minutes. The solvent is distilled under reduced pressure and the residue is dissolved in water (80 mL). The water solution is extracted with tert-butyl-methyl ether (3×80 mL) and the organic phase is removed. The water phase is evaporated under reduced pressure and the residue is re-dissolved in water (176 mL). Hydrochloric acid (6.53 mL of a 1M solution, 6.53 mmol) is added to precipitate the acid, followed by the addition of ethyl acetate (176 mL). The mixture is stirred for 15 min. and the layers are separated. The organic layer is washed with water (90 mL). Charcoal (0.5 g) is added to the organic layer and the mixture is stirred at 30-35° C. for several hours. Filter-aid (Cellflock, 1.0 g) is added and stirring is continued for additional 30 min. The charcoal is removed by filtration on a filter-aid to obtain a clear solution and the solvent is evaporated at 30-35° C. under reduced pressure, to obtain (E)-(3R,5S)-7-[2-Cyclopropyl-4-(4-fluoro-phenyl)-quinolin-3-yl]-3,5-dihydroxy-hept-6-enoic acid as a white solid. For the formation of the calcium salt, the acid (2.55 g, 6.05 mmol) is suspended in water (40.5 mL) and sodium hydroxide (0.260 g, 6.5 mmol) is added to obtain a clear solution of the corresponding sodium salt. A solution of calcium chloride (0.399 g, 3.49 mmol) in water (2 mL) is added dropwise to the solution of the sodium salt. A suspension is formed immediately upon addition of calcium chloride. The suspension is stirred for 4 hours at 20-25° C. and for 2 hours at 15-17° C. The product is isolated by filtration, the filter cake is washed with cold water and dried in vacuo at 20-25° C. to obtain (E)-(3R,5S)-7-[2-Cyclopropyl-4-(4-fluoro-phenyl)-quinolin-3-yl]-3,5-dihydroxy-hept-6-enoic acid, calcium salt as a white, crystalline powder, comprising 10.6% (w/w) water. $[\alpha]_D^\circ$=+22.92° (1:1 acetonitril/water, c=1). X-ray analysis revealed the presence of the crystal modification A. The ratio of the enantiomer having (3S, 5R) configuration was below the detection limit of 0.05% according to column electrophoresis. The product had more than 99.7 area % purity according to HPLC and comprised 0.09 area % of the corresponding epimers (sum of both the (3S,5S) and (3R, 5R) epimers, which were not separated in HPLC). The corresponding lactone could not be detected at a detection limit of 0.05 area %.

j)

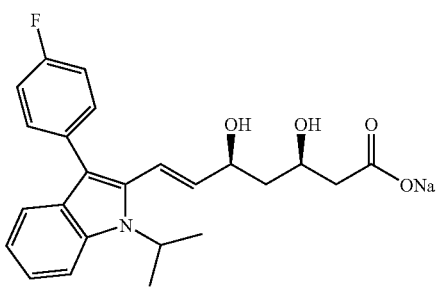

(E)-(3R,5S)-7-[3-(4-Fluoro-phenyl)-1-isopropyl-1H-indol-2-yl]-3,5-dihydroxy-hept-6-enoic acid sodium salt can be prepared from (E)-(3R,5S)-7-[3-(4-Fluoro-phenyl)-1-isopropyl-1H-indol-2-yl]-3,5-dihydroxy-hept-6-enoic acid ((S)-1-phenyl-ethyl)-amide by hydrolysis with sodium hydroxide according to the procedure described above for the preparation of (E)-(3R,5S)-7-[2-Cyclopropyl-4-(4-fluoro-phenyl)-quinolin-3-yl]-3,5-dihydroxy-hept-6-enoic acid. After completion of the hydrolysis, excess sodium hydroxide is neutralised by addition of hydrochloric acid and the solvent is evaporated under reduced pressure. As a work-up variant, the residue is dissolved in water at 60-70° C. and the solution is allowed to cool down to room temperature. Crystallisation occurs. The formed suspension is cooled down to 5° C., stirred for several hours at this temperature to complete the crystallisation and the product is isolated by filtration. (E)-(3R,5S)-7-[3-(4-Fluoro-phenyl)-1-isopropyl-1H-indol-2-yl]-3,5-dihydroxy-hept-6-enoic acid sodium salt is obtained as beige to yellow crystalline product.

The crystalline product can be dissolved in water and lyophilised to obtain a lyophilisate, which is soluble in organic solvents, e.g. in dichloromethane. $[\alpha]_D = -20°$ (c=0.8 in dichloromethane). The acid component of the salt is identical to the acid component of Fluvastatin® in none-chiral HPLC. IR and MS spectra of the product confirmed the proposed structure and were in accordance with published data for (E)-(3R,5S)-7-[3-(4-Fluoro-phenyl)-1-isopropyl-1H-indol-2-yl]-3,5-dihydroxy-hept-6-enoic acid sodium salt (see Tempkin et al., Tetrahedron 1997, 53, 10659-10670).

Alternatively, (E)-(3R,5S)-7-[3-(4-Fluoro-phenyl)-1-isopropyl-1H-indol-2-yl]-3,5-dihydroxy-hept-6-enoic acid sodium salt can be prepared by hydrolysis of (4R,6S)-6-{(E)-2-[3-(4-Fluoro-phenyl)-1-isopropyl-1H-indol-2-yl]-vinyl}-4-hydroxy-tetrahydro-pyran-2-one with NaOH.

k)

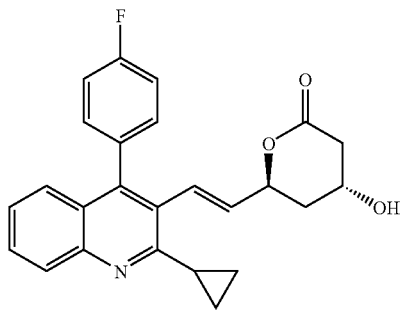

(4R,6S)-6-{(E)-2-[2-Cyclopropyl-4-(4-fluoro-phenyl)-quinolin-3-yl]-vinyl}-4-hydroxy-tetrahydro-pyran-2-one can be prepared as follows:

(E)-(3R,5S)-7-[2-Cyclopropyl-4-(4-fluoro-phenyl)quinolin-3-yl]-3,5-dihydroxy-hept-6-enoic acid ((S)-1-phenyl-ethyl)-amide (0.2 g, 0.381 mmol) is placed in a 3-necked, round bottomed flask and acetonitrile (10 mL) is added. The solution is treated with ortho-phosphoric acid (0.113 g, 1.14 mmol) and heated to 65-70° C. The reaction mixture is stirred for 18 h at 65-70° C. For work-up, the mixture is diluted with tert-butyl-methylether (30 mL) and the product solution is washed three times with water (3×30 mL). The organic layer is dried on anhydrous magnesium sulphate and the solvent is evaporated in vacuo to obtain 135.2 mg crude product as a colourless solid foam. The crude product is purified by column chromatography on silica gel with ethyl acetate/hexane fraction (7:3) as eluent. MS(ES+, m/z): 404 (MH+, 100%); IR(KBr): Strong absorptions at 3410, 1736, 1709, 1513, 1490, 1216, 1159, 1062, 1038, 970, 766 cm$^{-1}$. $^1$H-NMR confirmed the proposed structure.

l)

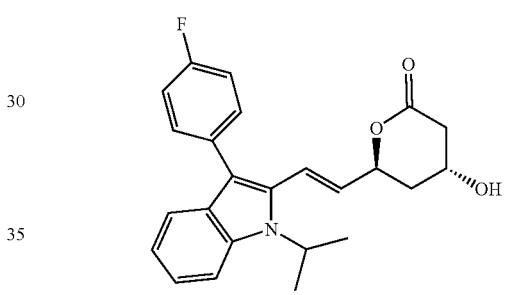

(4R,6S)-6-{(E)-2-[3-(4-Fluoro-phenyl)-1-isopropyl-1H-indol-2-yl]-vinyl}-4-hydroxy-tetrahydro-pyran-2-one can be prepared from (E)-(3R,5S)-7-[3-(4-Fluoro-phenyl)-1-isopropyl-1H-indol-2-yl]-3,5-dihydroxy-hept-6-enoic acid or its derivatives according to known procedures, see e.g. F. G. Kathawala, WIPO Patent WO 84/02131 (1984).

(m)

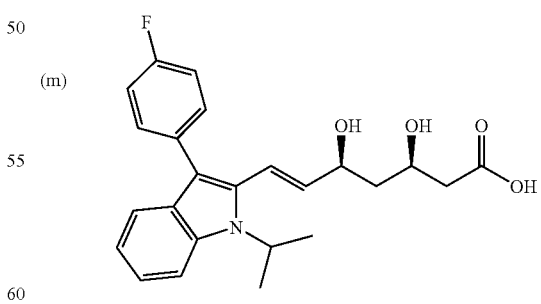

(E)-(3R,5S)-7-[3-(4-Fluoro-phenyl)-1-isopropyl-1H-indol-2-yl]-3,5-dihydroxy-hept-6-enoic acid can be prepared from the corresponding sodium salt [cf. (j)] by acid neutralisation e.g. with HCl and extraction with ethyl acetate which can be evaporated under vacuum.

What is claimed is:

1. A process for the manufacture of an enantiomerically pure form or a racemic form of a compound of formula

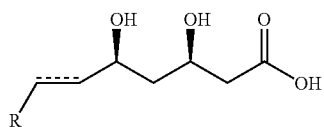

or a salt thereof, or a lactone thereof, wherein the element ·····represents —CH═CH—, and
R represents the cyclic residue of formula

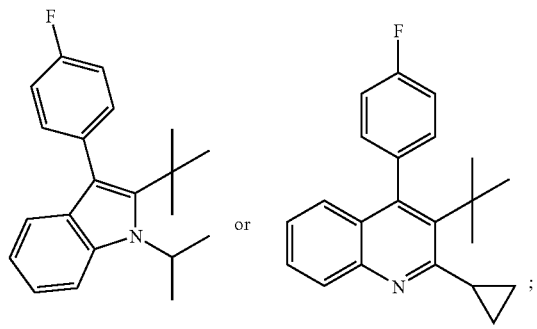

comprising
(a) reacting a compound of formula (III a) or (III b)

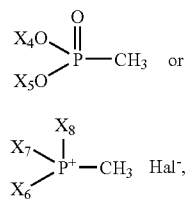

wherein $X_4$ and $X_5$, independently of one another, represents $C_1$-$C_7$-alkyl or phenyl-$C_1$-$C_7$-alkyl;
$X_6$, $X_7$, and $X_8$, independently of one another, represent phenyl that is unsubstituted or substituted by one or more substituents selected from the group consisting of $C_1$-$C_7$alkyl, hydroxy, $C_1$-$C_7$alkoxy, $C_2$-$C_8$alkanoyl-oxy, halogen, nitro, cyano, and $CF_3$; and Hal⁻ represents a halide anion;
with a metallated alkane to form the corresponding ylide and then reacting the resulting ylide intermediate with a compound of formula

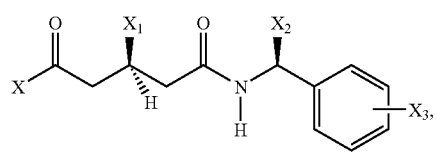

wherein
X represents etherified hydroxy, esterified hydroxy, or unsubstituted or mono- or di-substituted amino;
$X_1$ is protected hydroxy;
$X_2$ represents $C_1$-$C_7$alkyl; and
$X_3$ represents hydrogen or one or more substituents selected from the group consisting of $C_1$-$C_7$alkyl, hydroxy, $C_1$-$C_7$alkoxy, $C_2$-$C_8$alkanoyl-oxy, halogen, nitro, cyano, and $CF_3$, resulting in a compound of formula (III d)

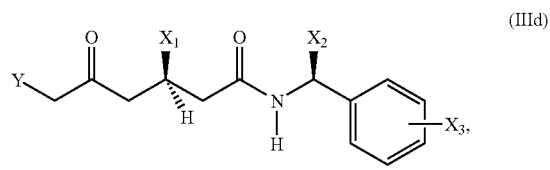

wherein $X_1$, $X_2$ and $X_3$ have the meanings as defined above, Y represents a group of formula $(X_4O)(X_5O)P(\!=\!O)$— or $(X_6)(X_7)(X_8)P^+$ Hal⁻, and $X_4$, $X_5$, $X_6$, $X_7$, $X_8$ and Hal⁻ have the meanings as defined above;
(c) reacting a compound of formula (III d) with an aldehyde of formula (III f) R—CH(═O) resulting in a compound of formula (III g')

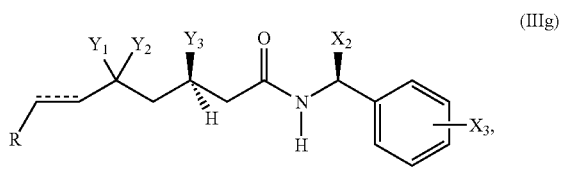

wherein R, $X_1$, $X_2$, $X_3$ and the element ·····have the meanings as defined above;
(e) converting a compound of formula (III g'), to a compound of formula (III i)

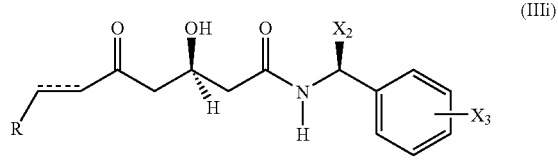

by removing the hydroxy protection group;
wherein R, $X_2$, $X_3$ and the element ·····have the meanings as defined above; and subsequent reduction of said compound of formula (III i) to a compound of formula (III h)

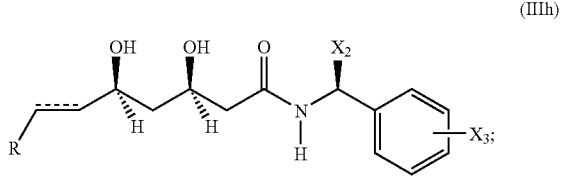

wherein R, $X_2$, $X_3$ and the element ·····have the meanings as defined above;

(f) hydrolyzing a compound of formula (III h) to a compound of formula (I) or a salt thereof;

(g) isolating a resulting compound of formula (I) or a salt thereof.

2. A process according to claim 1, wherein in formulae (III c), (III d), (III g'), (III h), and (III i), $X_2$ is methyl and $X_3$ is hydrogen.

3. A process according to claim 1, wherein in formula (III c), X is N—$C_1$-$C_7$alkyl-N—$C_1$-$C_7$alkoxy-amino.

4. A process according to claim 1, wherein in formulae (III c) and (III d) $X_1$ is tert-butyl-dimethyl-silyloxy, and in formulae (III g') and (III h), $Y_3$ is tert-butyl-dimethyl-silyloxy.

5. A process according to claim 1, wherein the salt is a pharmaceutically acceptable salt with a base.

6. A process for the manufacture of an enantiomerically pure form or a racemic form of a compound of formula

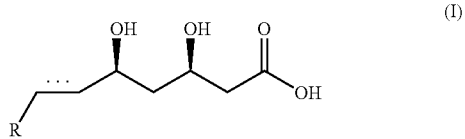

or a salt thereof, or a lactone thereof, wherein the element ⋯⋯ represents —CH=CH—, and R represents the cyclic residue of formula

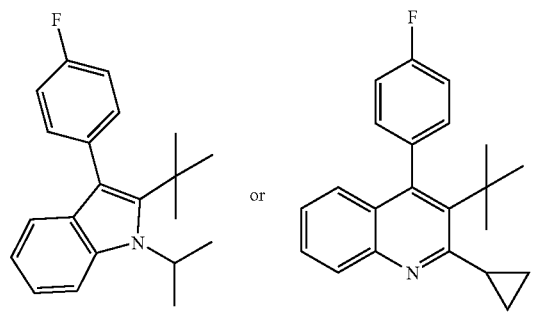

comprising (a) reacting a compound of formula (IIIa) or (IIIb)

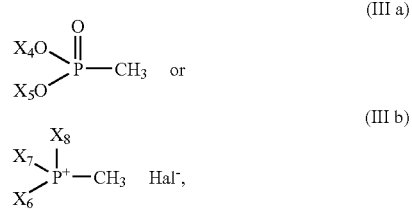

wherein $X_4$ and $X_5$, independently of one another, represents $C_1$-$C_7$-alkyl or phenyl-$C_1$-$C_7$-alkyl;

$X_6$, $X_7$, and $X_8$, independently of one another, represent phenyl that is unsubstituted or substituted by one or more substituents selected from the group consisting of $C_1$-$C_7$alkyl, hydroxy, $C_1$-$C_7$alkoxy, $C_2$-$C_8$alkanoyl-oxy, halogen, nitro, cyano, and $CF_3$; and Hal⁻ represents a halide anion;

with a metallated alkane to form the corresponding ylide and then reacting the resulting ylide intermediate with a compound of formula

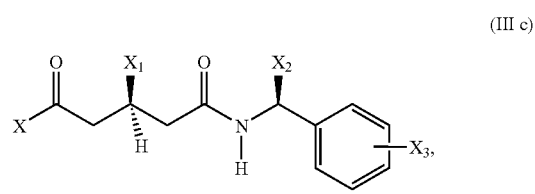

wherein

X represents etherified hydroxy, esterified hydroxy, or unsubstituted or mono- or di-substituted amino;

$X_1$ is protected hydroxy;

$X_2$ represents $C_1$-$C_7$alkyl; and $X_3$ represents hydrogen or one or more substituents selected from the group consisting of $C_1$-$C_7$alkyl, hydroxy, $C_1$-$C_7$alkoxy, $C_2$-$C_8$alkanoyl-oxy, halogen, nitro, cyano, and $CF_3$, resulting in a compound of formula (III d)

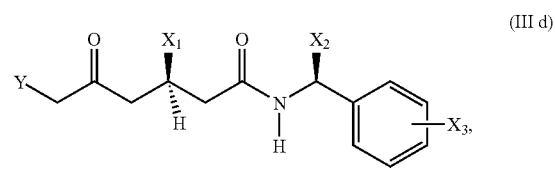

wherein $X_1$, $X_2$ and $X_3$ have the meanings as defined above, Y represents a group of formula ($X_4$O)($X_5$O)P(=O)— or ($X_6$)($X_7$)($X_8$)P⁺ Hal⁻, and $X_4$, $X_5$, $X_6$, $X_7$, $X_8$ and Hal⁻ have the meanings as defined above;

(b) converting a resulting compound of formula (III d) into a compound of formula (III e)

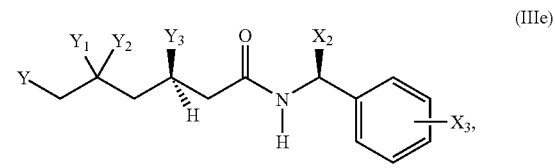

wherein $X_2$, $X_3$ and Y, have the meaning as defined above and wherein $Y_1$ represents hydroxy or protected hydroxy, $Y_2$ is hydrogen, $Y_3$ is hydroxy or protected hydroxy, and $Y_1$ and $Y_3$ form a syn-diol configuration; or wherein $Y_1$ and $Y_3$ together represent —O-Alk-O—, Alk being $C_1$-$C_7$alkylidene; $Y_2$ is hydrogen, and $Y_1$ and $Y_3$ form a syn-diol configuration;

(c) reacting a compound of formula (III e) with an aldehyde of formula (III f) R—CH(=O) resulting in a compound of formula (III g)

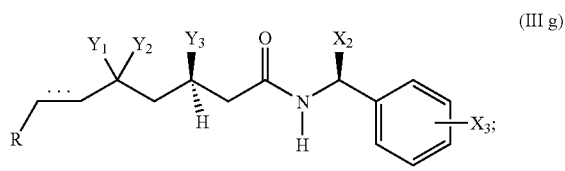

wherein R, $X_2$, $X_3$, $Y_1$, $Y_2$ and $Y_3$ and the element ⋯⋯ have the meanings as defined above;

(d) converting a compound of formula (III g), to a compound of formula (III h), by removing the hydroxy protection group(s)

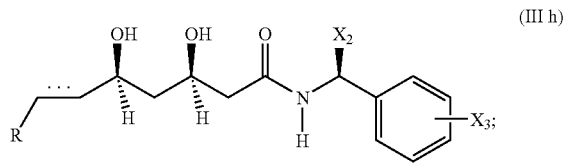

wherein R, $X_2$, $X_3$ and the element ⋯⋯ have the meanings as defined above;

(f) hydrolyzing a compound of formula (III h) to a compound of formula (I) or a salt thereof, (g) isolating a resulting compound of formula (I) or a salt thereof.

7. A process according to claim 6, wherein in formulae (III c), (III d), (III e), (III g) and (III h), $X_2$ is methyl and $X_3$ is hydrogen.

8. A process according to claim 6, wherein in formula (III c), X is N—$C_1$-$C_7$alkyl-N—$C_1$-$C_7$alkoxy-amino.

9. A process according to claim 6, wherein in formulae (III c) and (III d), $X_1$ is tert-butyl-dimethyl-silyloxy, and in formulae (III e), (III g) and (III h), $Y_3$ is tert-butyl-dimethyl-silyloxy.

10. A process according to claim 6, wherein the salt is a pharmaceutically acceptable salt with a base.

11. A process according to claim 1, which further comprises:

(h) one of (1) converting a resulting free acid of formula (I) into a salt thereof;

(2) converting a resulting free acid of formula (I) into a lactone of formula (I b) in the presence of an acid

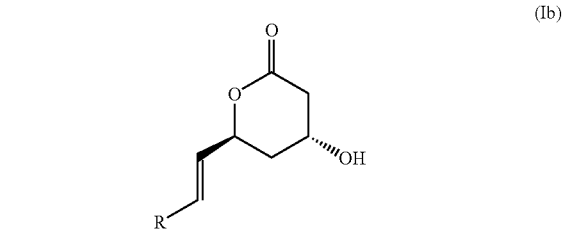

wherein R has the same meaning as defined in formula (I);

(3) converting a resulting free acid of formula (I) into a lactone of formula (I b) as defined above in the presence of an acid, and converting a resulting lactone of formula (I b) into an acid of formula (I) or a salt thereof in the presence of an alkali metal hydroxide.

12. A process according to claim 6, which further comprises:

(h) one of (1) converting a resulting free acid of formula (I) into a salt thereof;

(2) converting a resulting free acid of formula (I) into a lactone of formula (I b) in the presence of an acid

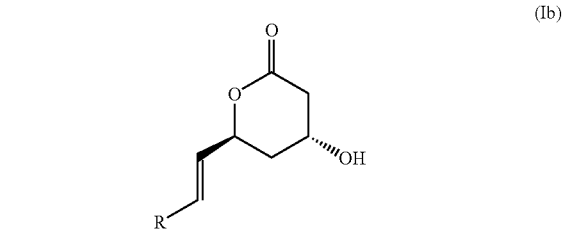

wherein R has the same meaning as defined in formula (I);

(3) converting a resulting free acid of formula (I) into a lactone of formula (I b) as defined above in the presence of an acid, and converting a resulting lactone of formula (I b) into an acid of formula (I) or a salt thereof in the presence of an alkali metal hydroxide.

* * * * *

UNITED STATES PATENT AND TRADEMARK OFFICE
CERTIFICATE OF CORRECTION

PATENT NO. : 7,371,865 B2 Page 1 of 1
APPLICATION NO. : 10/502177
DATED : May 13, 2008
INVENTOR(S) : Acemoglu et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by (315) days Delete the phrase "by 315 days" and insert -- by 364 days --

Signed and Sealed this

First Day of June, 2010

David J. Kappos
*Director of the United States Patent and Trademark Office*